United States Patent [19]

DeGraw et al.

[11] Patent Number: 5,354,751
[45] Date of Patent: Oct. 11, 1994

[54] HETEROAROYL 10-DEAZAAMINO-PTERINE COMPOUNDS AND USE FOR RHEUMATOID ARTHRITIS

[75] Inventors: Joseph I. DeGraw, Sunnyvale; William T. Colwell, Menlo Park, both of Calif.; Francis M. Sirotnak, New York, N.Y.; R. Lane Smith, Palo Alto, Calif.; James R. Piper, Birmingham, Ala.

[73] Assignee: SRI International, Menlo Park, Calif.

[21] Appl. No.: 90,750

[22] Filed: Jul. 12, 1993

Related U.S. Application Data

[63] Continuation-in-part of Ser. No. 28,431, Mar. 9, 1993, and a continuation-in-part of Ser. No. 8,919, Jan. 26, 1993, and a continuation-in-part of Ser. No. 938,105, Aug. 31, 1992, abandoned, and a continuation-in-part of Ser. No. 845,407, Mar. 3, 1992, abandoned, and a continuation-in-part of Ser. No. 875,779, Apr. 29, 1992, abandoned.

[51] Int. Cl.$^5$ .......................................... A61K 31/505
[52] U.S. Cl. .................... 514/249; 544/260; 544/279; 514/258
[58] Field of Search .................... 544/260; 514/249

[56] References Cited

U.S. PATENT DOCUMENTS

| | | | |
|---|---|---|---|
| 4,369,319 | 1/1983 | DeGraw et al. | 544/260 |
| 4,433,147 | 2/1984 | DeGraw | 544/260 |
| 4,988,813 | 1/1991 | Taylor et al. | 544/279 |
| 5,026,851 | 6/1991 | Taylor et al. | 544/279 |
| 5,030,634 | 7/1991 | Krumdieck et al. | 514/249 |
| 5,260,296 | 11/1993 | Nair et al. | 544/260 |

OTHER PUBLICATIONS

Washington Post, Apr. 16, 1992, p. A-14.

*Primary Examiner*—Donald G. Daus
*Attorney, Agent, or Firm*—Hana Dolezalova

[57] ABSTRACT

There is disclosed certain heteroaroyl 10-deazaaminopterin and 5, 10 and 8, 10 di deazaminopterin compounds and their use for treatment of rheumatoid arthritis and related diseases and preparative process.

Also disclosed are 10 alkenyl-(and alkynyl) 10-deazaminopterins also disclosed for treatment of rheumatoid arthritis and for leukemia and ascites tumors and preparative process.

13 Claims, No Drawings

HETEROAROYL 10-DEAZAAMINO-PTERINE COMPOUNDS AND USE FOR RHEUMATOID ARTHRITIS

This application is a continuation-in-part of the U.S. patent application for "Process for Preparing 10-Deazaaminopterins and 5,10- and 8,10-Dideazaaminopterins from Pteroic Dicarboxylic Acid Diesters" Ser. No. 08/028,431 pending filed on Mar. 9, 1993 and of the U.S. patent application for "Heteroaroyl-10-Deazaaminopterins and 5,10-Dideazaaminopterins for Treatment of Inflammation" Ser. No. 08/008,919 pending filed on Jan. 26, 1993 and of the U.S. patent application for "Heteroaroyl-10-deazaaminopterins for Treatment of Inflammation" Ser. No. 07/938,105 filed on Aug. 31, 1992 now abandoned and of the U.S. patent application for "10-Alkenyl and 10-Alkynyl-10-Deazaaminopterins," Ser. No. 07/845,407 filed on Mar. 3, 1992, now abandoned and of the U.S. patent application for "5-Deazaaminopterins and 5,10-Dideazaaminopterins for Treatment of Inflammation, Ser.No. 07/875,779 filed on Apr. 29, 1992, now abandoned.

BACKGROUND OF THE INVENTION

1. Field of the Invention

The current invention concerns novel antiinflammatory and antineoplastic 10-deazaaminopterin compounds. In particular, the invention concerns heteroaroyl-10-deazaaminopterins and 10-alkenyl or 10-alkynyl-10-deazaaminopterins having pronounced antiinflammatory activity, antileukemic and antitumorigenic activity, as well as a method for treatment of inflammatory diseases, leukemia and tumors. Pharmaceutical compositions containing these heteroaroyl-10-deazaaminopterin compounds are also disclosed. The invention further concerns a process for preparation of these compounds.

BACKGROUND OF THE INVENTION AND RELATED DISCLOSURES

Rheumatoid arthritis, malignant tumors and leukemia are severely debilitating diseases which are often fatal, as in cases of leukemia and malignant growths. Drugs which are currently available and used for treatment of these diseases typically have unpleasant secondary symptoms or are highly toxic.

Rheumatoid arthritis is one of a number of forms of proliferative disease, and the development of drugs for amelioration or curing the disease has occupied the attention of research organizations for many years, until most recently without appreciable success.

Rheumatoid arthritis is an inflammation of the joints arising from infectious, metabolic, or constitutional causes, usually of unknown origin. In its advanced stage it is debilitating, as it can result in serious restriction of movement and even invalidism. Since rheumatoid arthritis is a common disease that affects 2-3 million people in the United States alone, it poses a serious health problem. With disease progression, a substantial proportion of affected individuals develops erosive joint disease and despite therapies including disease-modifying antirheumatic drugs such as gold complexes, penicillamine, antimalarials, and methotrexate often require surgical joint replacement. In some patients with intractable rheumatoid arthritis, administration of immunosuppressive agents including azathioprine, methotrexate, cyclophosphamide, and combinations of these drugs have been proven beneficial. However, the actual or potential side effects of some of these drugs, including bone marrow toxicity and neoplasia, have limited the frequency and the dose at which they can be administered.

Leukemia is an acute or chronic disease of unknown cause which is characterized by malignant neoplasm of the blood forming tissues in man and other warm-blooded animals. It is characterized by an abnormal increase in the number of immature leukocytes in the tissues of the body and in the circulating blood. The disease apparently affects the blood-forming organs, and is classified according to the type of leukocyte that is being proliferated abnormally. The disease is one of a number of forms of neoplastic disease, and the development of drugs for amelioration or curing the disease has been of great interest. Today, many forms of leukemia can be effectively treated with drugs. In the case of combination chemotherapy with acute lymphocytic leukemia in children, a large percentage, (50-60%) of five year survivals are obtained, and the disease is now classified as curable.

Malignant tumors result from a cellular malignancy whose unique characteristics—loss of normal cellular controls and regulations—results in unregulated growth, lack of differentiation, and ability to invade local tissues and metastasize.

There is no effective treatment of malignant growths aside from radical surgery. Once, however, the tumor metastasizes, the only therapies which are somewhat effective are radio and chemotherapy. Both these therapies have severe side-effects which make them very unpleasant.

It would thus be extremely useful to provide therapies for rheumatoid arthritis, leukemia and malignant tumors with drugs which would be less toxic and still be effective in treatment of these diseases.

The antifolic acid drug, methotrexate, has been used as an antitumor agent since 1955. Its cytotoxic action in tumors is related to its ability to inhibit, essentially irreversibly, the key enzyme, dihydrofolate reductase, required for biosynthesis of tetrahydrofolic acid. Tetrahydrofolate is a vital component in one-carbon metabolism in cells, being required for biosynthesis of purine and pyrimidine nucleosides of the DNA and RNA. The drug is a powerful cytotoxic agent whose principal toxicities occur with liver, kidney, and mucosal tissue. Liver toxicity is the paramount concern for use in chronic therapy in a disease such as arthritis.

The ability of methotrexate to affect the inflammatory conditions of rheumatoid arthritis may be linked to its cytotoxic behavior. This may be in the nature of immune suppression and could involve attack on inflammatory phagocytic cells such as macrophages or neutrophils and T-helper cells in the synovial region. Very few methotrexate analogues have been evaluated against arthritis in animals, and there is no clear indication whether the antiarthritic properties are directly proportional to cytotoxicity. Studies published in *Chem. Biol. Pteridines*, 847 (1986) DeGuyter, Berlin, showed that adjuvant arthritis and streptococcal cell wall arthritis in rats responded to doses of methotrexate which were in good correlation to those used in man for treatment of rheumatoid arthritis and that timing and dosage were both important for reduction of inflammation. Both methotrexate and aminopterin were found to inhibit inflammation, but other antifolate compounds that did not possess a 2,4-diaminopyrimidine unit or a benzoylglutamate side chain were ineffective.

In 1974, *J. Med. Chem.,* 17:552, reported the synthesis and antifolate activity of 10-deazaaminopterin. The antimicrobial and antitumor activities of the powerful dihydrofolic reductase inhibitors aminopterin and its N-10 methyl derivative, methotrexate, are well known, and numerous analogues have been made to further improve the potency, cell penetration and toxicity properties of these compounds.

U.S. Patent No. 4,369,319, issued Jan. 19, 1983, discloses 10-deazaaminopterin compounds having the following structure:

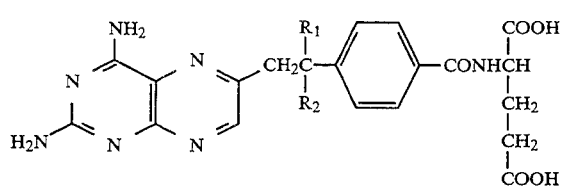

wherein $R_1$ and $R_2$ are both hydrogen or alkyl having from one to about eight, preferably one or two carbon atoms, or when only one of $R_1$ and $R_2$ is alkyl, and the other is hydrogen.

These alkyl derivatives were found active against leukemia as well as against other malignancies, including ascitic tumors, which can be ameliorated in warm-blooded lower animals by the administration of 10-deazaaminopterin. The use of deazaaminopterin as antirheumaticum is described in the use U.S. Pat. No. 5,030,634. The sole compound described in the '634 patent is identical to the compound, described in U.S. Pat. No. 4,369,319, wherein both $R_1$ and $R_2$ are hydrogens.

Other derivatives of methotrexate, namely pyrido[2,3-] pyrimidines disclosed in U.S. patent No. 5,026,851 were found to be active against neoplastic growth. The process to prepare these compounds is disclosed in the U.S. Pat. No. 4,988,813.

It is therefore a primary object of this invention to provide an effective treatment for inflammatory diseases, such as rheumatoid arthritis as well as an effective drug for inhibition of malignant neoplasms of the blood forming tissues and for inhibition of growth of malignant tumors with compounds, which exhibit relatively low toxicity compared to current treatments.

All references cited herein and in the following text are hereby incorporated by reference in their entirety.

SUMMARY

One aspect of the current invention is heteroaroyl-10-deazaaminopterin compounds of formula (I)

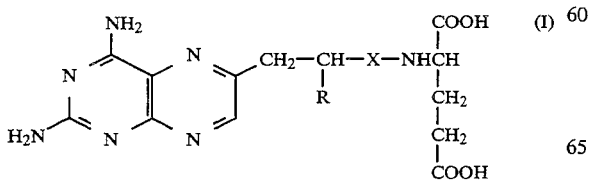

wherein X is selected from

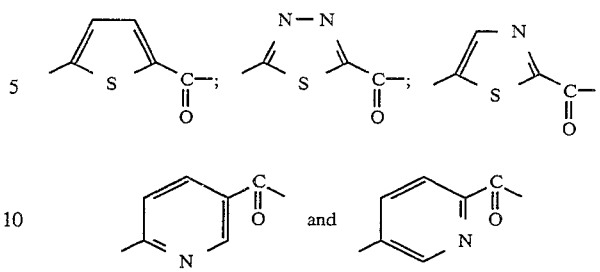

and R is hydrogen or alkyl, alkenyl, or alkynyl having from one to about eight carbon atoms, preferably from one to one carbon atoms for alkyl and three to five carbon atoms for alkenyl and alkynyl.

Another aspect of the current invention is a method for treatment of rheumatoid arthritis by administering to a patient in need of such treatment an effective amount of the compound of formula (I) or its pharmaceutically acceptable salt.

Still another aspect of the current invention is a method for inhibition of malignant neoplastic growth of the blood forming tissue or malignant tumor growth of other tissues by administering to a patient in need of such treatment an effective amount of the compound of formula (I) or its pharmaceutically acceptable salt.

Still another aspect of the current invention is 10-alkenyl-10-deazaaminopterin and 10-alkynyl-10deazaaminopterin compound of formula (II)

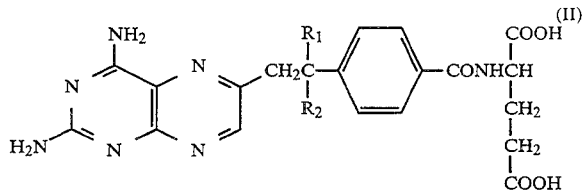

wherein $R_1$ and $R_2$ are selected from the group consisting of hydrogen, alkynyl and alkenyl having from one to about eight, preferably three to five carbon atoms.

Another aspect of the current invention is a method for treatment of rheumatoid arthritis by administering to a patient in need of such treatment an effective amount of the compound of formula (II) or its pharmaceutically acceptable salt.

Still another aspect of the current invention is a method for inhibition of malignant neoplastic growth of the blood forming tissue or malignant tumor growth of other tissues by administering to a patient in need of such treatment an effective amount of the compound of formula (II) or its pharmaceutically acceptable salt.

Still yet another aspect of the current invention is a process for preparing compounds of formula (I).

The final aspect of the current invention is a process for preparing compounds of formula (II).

DETAILED DESCRIPTION OF THE INVENTION

The current invention concerns novel 10-deazaaminopterin compounds which are nontrivial analogues of methotrexate and which are either as effective or more effective in treatment of rheumatoid arthritis or for inhibition of malignant neoplastic growth.

The invention also provides a method of treating arthritis and other proliferative diseases, as well as inhibiting malignant neoplastic growth, which method comprises administering to a warm-blooded animal having an inflammation of the joints or other evidence of the disease or suffering from leukemia or tumorigenic growth, a therapeutic nontoxic amount of a 10-deazaaminopterin compound or a pharmaceutically acceptable salt thereof. These salts are formed with one or more free NH2 groups and/or COOH groups of the 10-deazaaminopterin compound.

I. Heteroaroyl-10-Deazaaminopterins

In accordance with the present invention, heteroaroyl-10-deazaaminopterins are compounds of formula I

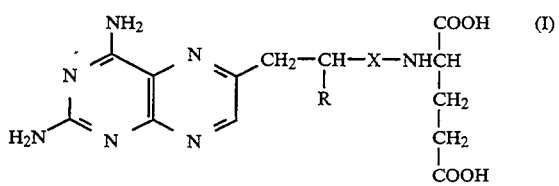

wherein X is one of

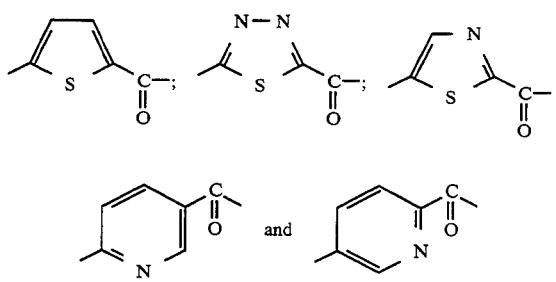

and R is hydrogen or alkyl, alkenyl, or alkynyl having from one to about eight carbon atoms, preferably from one to three carbon atoms for alkyl and three to five carbon atoms for alkenyl and alkynyl.

Exemplary alkyl substituent includes methyl, ethyl, propyl, iso-propyl, butyl, isobutyl, sec-butyl, tert-butyl, amyl, iso-amyl, sec-amyl, tert-amyl, hexyl, iso-hexyl, heptyl, iso-heptyl, octyl, iso-octyl, 2-ethyl hexyl, and tert-octyl.

Exemplary alkenyl substituent includes allyl, crotyl (2-butenyl), 2-pentenyl, 2-pentenyl, 2-hexenyl, 2-hexenyl, 3-isopropenyl, 3-isobutenyl, and 2-octenyl.

Exemplary alkynyl substituent includes propargyl, 2-butynyl, 3-butynyl, 2-pentynyl, 2-hexynyl, and 2-octynyl.

A subclass of pyridyl compounds within the scope of the invention is defined by formula IA

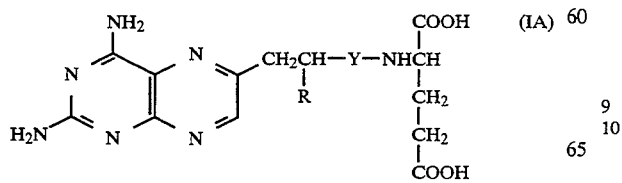

wherein Y is selected from

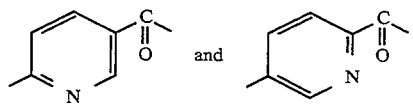

and R is hydrogen or alkyl, alkenyl, or alkynyl having from one to about eight carbon atoms, preferably from one to three carbon atoms for alkyl and three to five carbon atoms for alkenyl and alkynyl.

One subclass of thienyl compounds and thienyl analogues within the scope of the invention is defined by formula IB

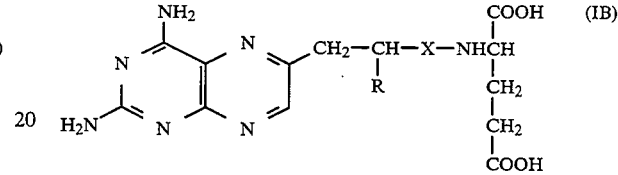

wherein Y is selected from

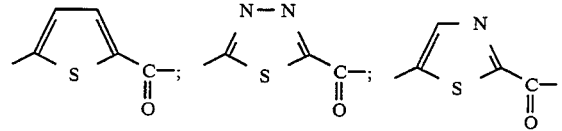

and R is hydrogen or alkyl, alkenyl, or alkynyl having from one to about eight carbon atoms, preferably from one to three carbon atoms for alkyl and three to five carbon atoms for alkenyl and alkynyl.

Exemplary heteroaroyl-10-deazaaminopterin compounds falling within the scope of the formula IA and IB are shown in the Table 1.

TABLE 1

| Compound # | $R_1$ | X |
|---|---|---|
| 1 | H | |
| 2 | $C_2H_5$ | (pyridyl carbonyl) |
| 3 | H | |
| 4 | $C_2H_5$ | (pyridyl carbonyl) |
| 5 | H | |
| 6 | $C_2H_5$ | (thienyl carbonyl) |
| 7 | H | |
| 8 | $C_2H_5$ | (thiadiazolyl carbonyl) |
| 9 | H | |
| 10 | $C_2H_5$ | (thiazolyl carbonyl) |

TABLE 1-continued

| Compound # | R₁ | X |
|---|---|---|
| 11 | CH₃ | (5-methyl-2-thienyl)C(=O)– |
| 12 | CH₃ | (5-methyl-1,3,4-thiadiazol-2-yl)C(=O)– |
| 13 | CH₃ | (5-methylthiazol-2-yl)C(=O)– |
| 14 | CH₃ | (6-methylpyridin-3-yl)C(=O)– |
| 15 | CH₃ | (5-methylpyridin-2-yl)C(=O)– |
| 16 | C₃H₇ | (5-methyl-2-thienyl)C(=O)– |
| 17 | i-C₃H₇ | |
| 18 | n-C₄H₉ | |
| 19 | CH₂=CH—CH₂— | |
| 20 | CH≡CCH₂ | |
| 21 | C₅H₁₁ | |
| 22 | C₈H₁₇ | |
| 23 | C₃H₇ | (6-methylpyridin-3-yl)C(=O)– |
| 24 | i-C₃H₇ | |
| 25 | n-C₄H₉ | |
| 26 | CH₂=CH—CH₂— | |
| 27 | CH≡CCH₂ | |
| 28 | C₅H₁₁ | |
| 29 | C₈H₁₇ | |
| 30 | C₃H₇ | (5-methylpyridin-2-yl)C(=O)– |
| 31 | i-C₃H₇ | |
| 32 | n-C₄H₉ | |
| 33 | CH₂=CH—CH₂— | |
| 34 | CH≡CCH₂ | |
| 35 | C₅H₁₁ | |
| 36 | C₈H₁₇ | |
| 37 | C₃H₇ | (5-methyl-1,3,4-thiadiazol-2-yl)C(=O)– |
| 38 | i-C₃H₇ | |
| 39 | n-C₄H₉ | |
| 40 | CH₂=CH—CH₂— | |
| 41 | CH≡CCH₂ | |
| 42 | C₅H₁₁ | |
| 43 | C₈H₁₇ | |
| 44 | C₃H₇ | (5-methylthiazol-2-yl)C(=O)– |
| 45 | i-C₃H₇ | |
| 46 | n-C₄H₉ | |
| 47 | CH₂=CH—CH₂— | |
| 48 | CH≡CCH₂ | |
| 49 | C₅H₁₁ | |
| 50 | C₈H₁₇ | |

II. Preparation of Heteroaroyl-10-Deazaaminopterins

Heteroaroyl-10-deazaaminopterins are prepared by processes described in following reaction schemes 1–4. The compounds of Formula IA, wherein X is

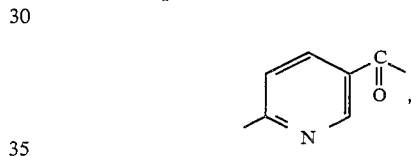

are synthesized by the procedure illustrated in Reaction Scheme 1.

Reaction Scheme 1

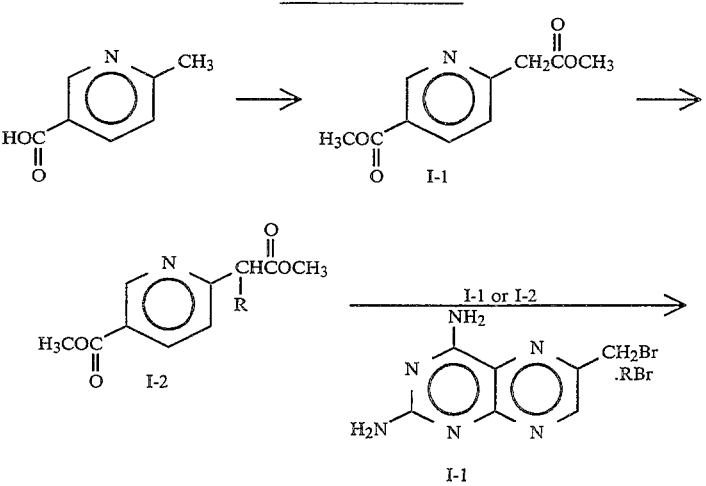

Reaction Scheme 1

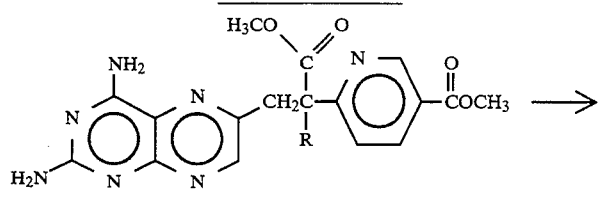

I-3a: R = H
I-3b: R = CH₂CH₃

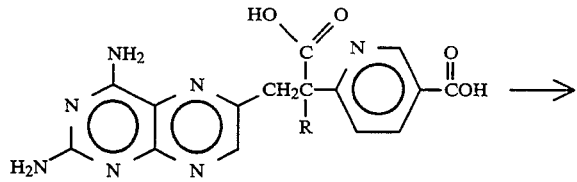

I-4a: R = H
I-4b: R = CH₂CH₃

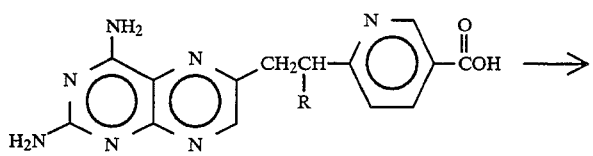

I-5a: R = H
I-5b: R = CH₂CH₃

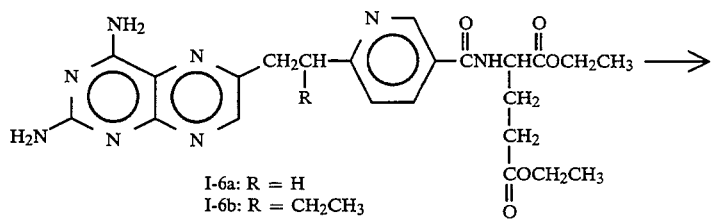

I-6a: R = H
I-6b: R = CH₂CH₃

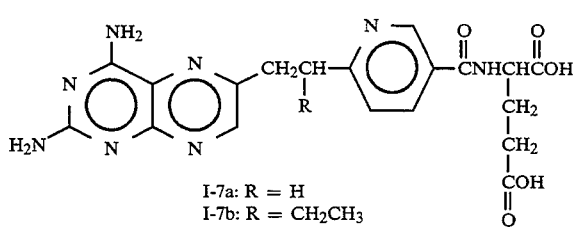

I-7a: R = H
I-7b: R = CH₂CH₃

Reaction Scheme 2 illustratesoa preparation of pyridyl compounds wherein X is

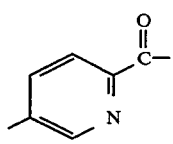

by substituting a starting compound in the Reaction Scheme 1 with compound of the formula

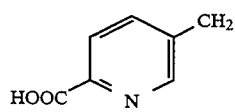

used as a starting compound in the Reaction Scheme 2. The synthetic process illustrated in Reaction Scheme 2 differs from procedures illustrated in Reaction Scheme 1 at intermediate steps II-2 to II-5 because it is necessary to use the pyridine carboxylate protected as an ester to prevent its decarboxylation in the step II-5 to II-6

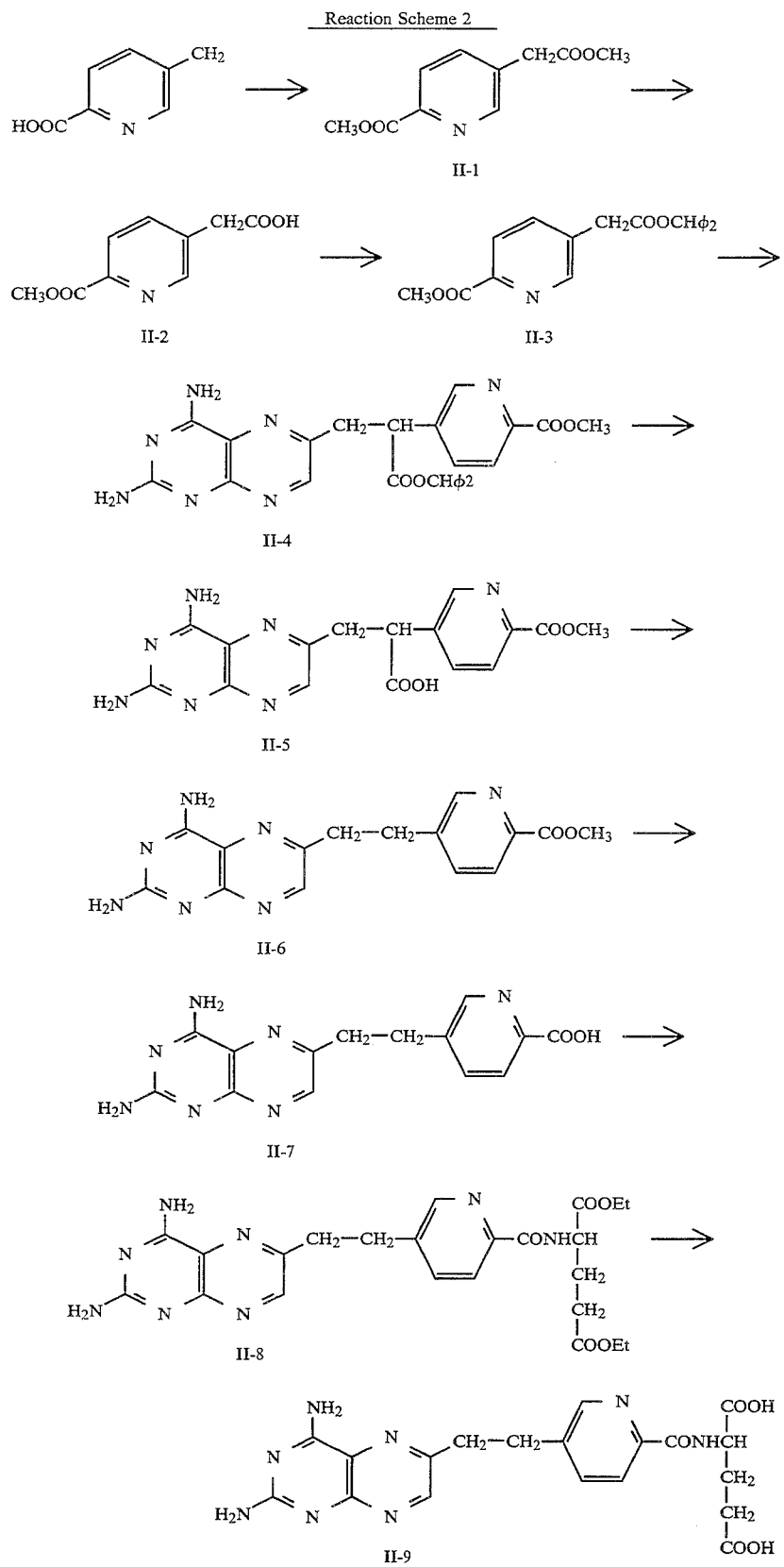
The following procedure illustrated in Reaction Scheme 3 is used to prepare thiophene analogues of compound of formula I.

Reaction Scheme 3

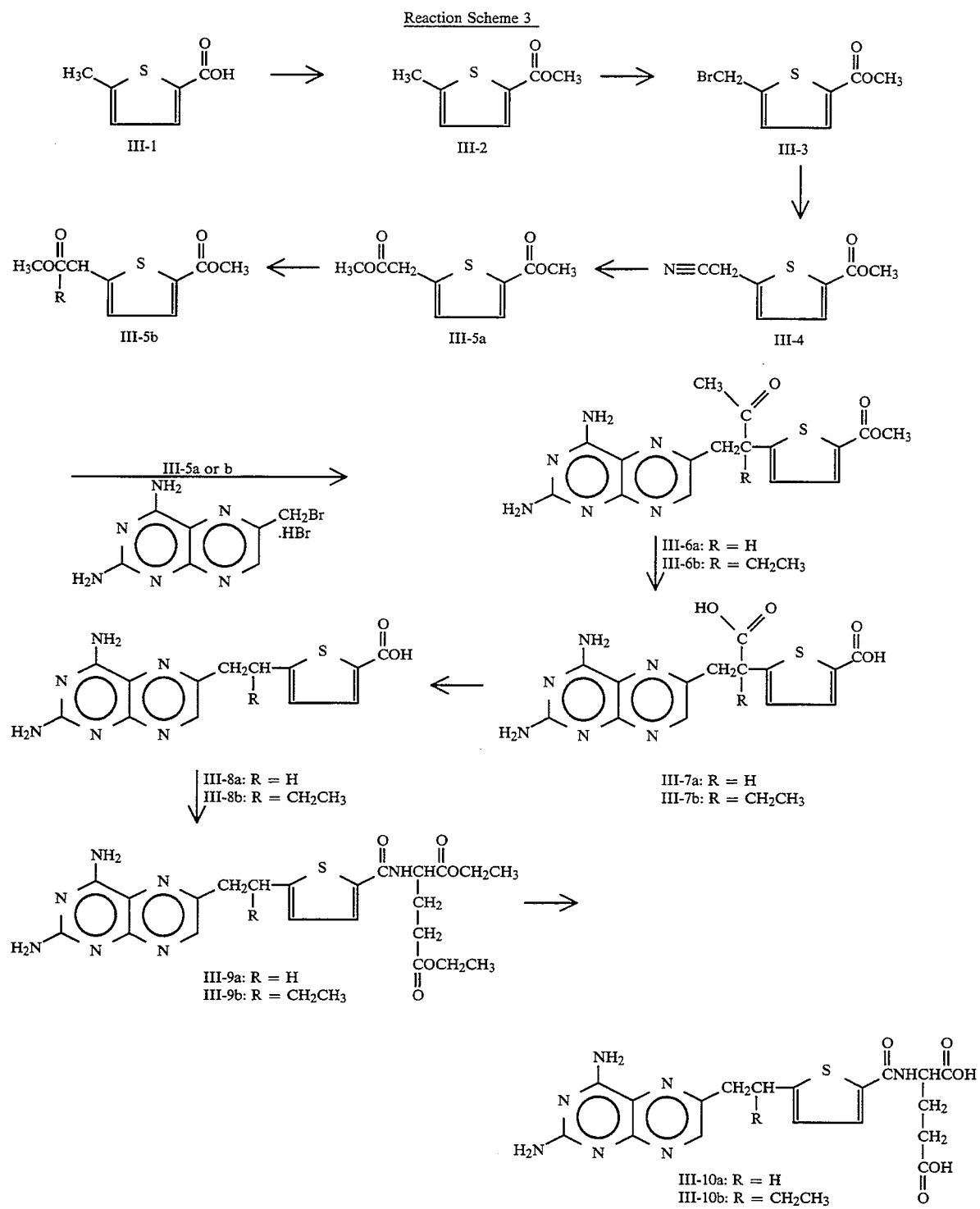

The same procedure suitable to prepare analogues of 10-deazaaminopterins wherein X is thiophene, illustrated in the Reaction Scheme 3, is used to prepare thiazole or thiadiazole analogues of 10-deazaaminopterins of formula I.

An alternative procedure shown in Reaction Scheme 3a can be used to substitute a process for preparation of thiophene dimethyl ester II 5a in Reaction Scheme 3.

Reaction Scheme 3a

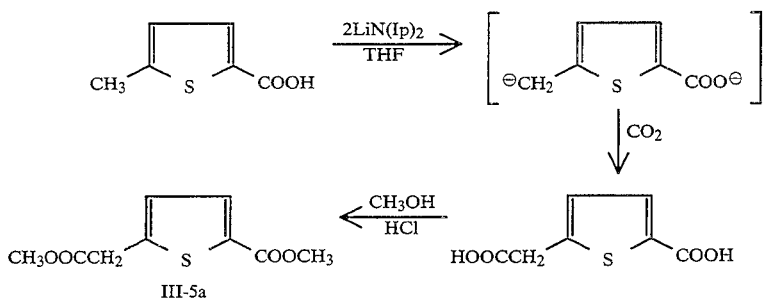

Heteroaroyl-10-deazaaminopterins wherein the substituent Y is 2-pyridyl is prepared by treating diisopropylamine dissolved in dry tetrahydrofuran with n-butyl lithium dissolved in an organic solvent such as hexane, pentane, heptane, or octane, and stirred at 0° C. for about 1 hour. The lithium diisopropyl amide solution is added dropwise over 15°90 min to a −25° C. mixture of 6-methylnicotinic acid and hexamethylphosphorous triamide in dry tetrahydrofuran. The temperature of the red solution is allowed to rise to about 0° C. with continuous stirring for 2 h. Carbon dioxide is bubbled through the 0° C. solution. The mixture is allowed to rise to room temperature and is stirred for another 8–24 hours. Filtration gives a solid which is suspended in an alcohol, preferably in methanol, the mixture is cooled to about 0° C. and acidified with preferably methanolic hydrochloric acid. After stirring for 1–5 days, preferably for 3 days, the mixture is concentrated and partitioned between organic and aqueous solvent, preferably between ether and saturated sodium bicarbonate. The organic layer is washed, rinsed and dried to yield product compound I-1, namely 5-carboxymethoxy-2-pyridylacetic acid methyl ester.

To a suspension of sodium hydride in dry dimethyl formamide is added a solution of I-1 in an organic solvent such as dry dimethyl formamide. The mixture is stirred at around 0° C. for 30–90 minutes, preferably for 60 minute, then cooled to about −30° C. A solution of ethyl iodide in dry dimethyl formamide is added dropwise, maintaining a reaction temperature of about −25° C. The mixture is then stirred for 1–4 hours, preferably for 2 hours at room temperature. The reaction is neutralized to about pH 8 by adding solid carbon dioxide, and the product is then concentrated under high vacuum. The residue is partitioned between ether and water, the organic layer is washed with preferably mixture of 10% sodium bicarbonate, 10% sodium bisulfite, and water. The organic layer is dried and concentrated to a pale brown oil, α-ethyl-5-carbomethoxy-2-pyridylacetic acid methyl ester (I-2).

A solution of I-1 dissolved in dry dimethyl formamide is added to a suspension of sodium hydride dissolved in dry dimethyl formamide. The mixture is stirred at around 0° C. for 10–60 minutes, preferably for 30 min, then cooled to about −30° C. A solution of 2,4-diamino-6-bromomethylpteridine hydrobromide dissolved in dry dimethyl formamide is slowly added dropwise over about 40 min. The reaction is stirred for about 2.5 h at 5°–20° preferably at 10° C., and the pH is adjusted to pH 8 by adding dry ice. The mixture is concentrated under high vacuum to give a solid, 3-(2,4-diaminopyrimido[4,5-b]pyrazin-6-yl)-2-(3-carbomethoxypyrid-6-yl)-propionic acid methyl ester (I3a).

A solution of the ester I-3a dissolved in an alcohol, such as 2-methoxyethanol, water, and a base such as 10% sodium hydroxide is stirred for 1–4 hours, preferably for 2.5 hours and then diluted with water. The pH of the reaction is adjusted to pH 6 with an acid, preferably with glacial acetic acid. The cream-colored precipitate is collected, and dried to yield the dicarboxylic acid I-4a.

A mixture of the dicarboxylic acid I-4a in dry argon-purged dimethyl sulfoxide is heated to 90–130, preferably to 110° C. for 15–60 minutes, preferably for 25 min, then concentrated under high vacuum. The residue is suspended in an aqueous solvent, preferably in water and sufficient base such as ammonium hydroxide is added to produce a solution. The solution is adjusted to about pH 5 by dropwise addition of an acid, such as glacial acetic acid, to yield the product β-(2,4-diamino-[4,5-β]pyrazin-6-yl)-6-ethylnicotinic acid (I-5a).

A mixture of the carboxylic acid (I-5a) dissolved in an organic solvent such as dry dimethyl formamide is treated with a base such as triethylamine under stirring for 30–90 minutes, preferably for 1 hour and the mixture is treated with isobutyl chloroformate. The mixture is further stirred for 30–90 minutes, preferably for 1 hour at room temperature and treated with L-glutamic acid diethyl ester hydrochloride. After about 1–3 hours, preferably 2 hours, the mixture is again treated one or more times with isobutyl chloroformate followed by L-glutamic acid diethyl ester hydrochloride and concentrated under high vacuum followed by digestion with ether and water to afford product N-[beta-(2,4-diaminopyrimido-[4,5-β]-pyrazin-6-yl)-6-ethylnicotinoyl]-glutamic acid diethyl ester (I-6a).

Diester (I-6a) is dissolved in an alcohol solvent such as 2-methoxyethanol and a strong base such as 10% sodium hydroxide and water and stirred at room temperature for about 2–4 hours. The solution is then diluted with water, adjusted to pH 6 with an acid, such as acetic acid, and filtered to give the product N-[beta-(2,4-diaminopyrimido[4-5-beta-]-pyrazin-6-yl)-6-ethylnicotinoyl-] glutamic acid compound (I-7a). This compound is shown as compound 1 in the Table 1.

Other variations of pyridyl compounds are prepared in the same way including modifications which may be necessary depending on the target product.

Preparation of compounds according to the Reaction Scheme 2 is typically as follows.

2-Carbomethoxy-5-pyridylacetic acid methylester (II-1) is prepared from 5-methylpicolinic acid in a manner similar to preparation of compound I-1.

A solution of a strong base, such as potassium hydroxide in an aqueous alcohol, such as 90% methanol is treated with a solution of compound II-1 in an alcohol, preferably methanol. After about 2 hours, the pH of the solution is adjusted to pH 6.5 by addition of hydrochloric acid. The solution is concentrated in vacuo to give a solid that is a mixture of both monoesters, the dicarboxylic acid and the starting diester. The desired monoester (II-2) represents a major component of the mixture.

The mixture (II-2) in chloroform is cooled to about 0° C. and treated dropwise with a solution of diphenyldiazomethane dissolved in an organic solvent such as chloroform. The resulting mixture is stirred at ambient temperature for about 24 hours. The solution is washed with saturated sodium bicarbonate and water and the organic layer is dried, preferably over magnesium sulfate to give the product 2-carbomethoxy-5-pyridylacetic acid benzhydryl ester (II-3).

A cold suspension of sodium hydride in dry N,Ndimethylformamide was treated dropwise with a solution of II-3 in an organic solvent such as dry dimethylformamide. The mixture is stirred at about 0° C. for about 2 hours, cooled to about −25° C. and treated, dropwise with a solution of 2,4-diamino-6-bromomethylpteridine hydrobromide in dry dimethylformamide with maintenance of the temperature at −25° C. The mixture is stirred at about 20°–25° C. for about 2.5 hours, adjusted to about pH 8 by addition of dry ice concentrated in vacuo, washed with ether and water and dried to yield the product 3-(2,4-diaminopyrimido[4,5-betapyrazin-6-yl)-2-(2-carbomethoxypyrid-5-yl)propionic acid benzhydryl ester (II-4).

A mixture of the diester II-4 in dichloromethane is treated with an acid such as 99% trifluoroacetic acid. The solution is kept at room temperature for 15–90, preferably for 50 minutes, then concentrated at room temperature under vacuum. The residue is washed repeatedly with ether then dried in vacuo giving a solid. The solid is suspended in water and neutralized to about pH 6–7 with 1.5M ammonium hydroxide. The product is collected by filtration and dried to give monocarboxylic acid II-5.

A solution of the monocarboxylic acid, II-5 dissolved in dimethylsulfoxide is stirred at a temperature of about 130° for about 30 minutes. The solution is concentrated under high vacuum and the residue was washed with ether and water. The solid is collected and dried in vacuo at room temperature to afford beta-[3-(2,4-diaminopyrimido[4,5-B]-pyrazin-6-yl)]-4-ethylpicolinic acid methyl ester (II-6).

A mixture of the ester II-6 dissolved in an alcohol, such as 2-methoxyethanol is treated with water and then with a strong base such as 10% sodium hydroxide. After stirring for about 45 min, the solution is neutralized to a pH of about 7.5 with hydrochloric acid and concentrated under high vacuum to afford the product beta-[3-(2,4diaminopyrimido[4,5B]-pyrazin-6-yl)]-4-ethyl picolinic acid (II-7).

A mixture of the carboxylic acid (II-7) and an amine such as triethylamine, and dry dimethyl formamide is stirred at room temperature for about 15 min. Isobutyl chloroformate is added and the mixture is stirred for about 1 hour. L-Glutamic acid diethyl ester hydrochloride is added and the mixture is stirred for about 2 hours. The addition of isobutyl chloroformate and diethyl glutamate is repeated at about one-half the initial quantities and the final mixture is stirred for about 16 hours. After filtration, the filtrate is concentrated in vacuo to yield the diester beta-[3-(2,4)-diaminopyrimido (4,5-b)-pyrazin-6-yl)]-4-ethylpicolinoyl]glutamic acid diethyl ester (IIS).

The diester (II-8) is dissolved in an alcohol such as 2-methoxyethanol and 10% sodium hydroxide is added. The mixture is stirred for about 2 hours at room temperature. The pH of the solution is adjusted to about pH 5–6 with acetic acid and evaporated in vacuo. The residue is treated with water , adjusted to pH 3–4 and the product is collected to give beta-[3-(2,4)-diaminopyrimido[4,5-B]-pyrazin-6-yl]-4-ethyl-picolinoyl]glutamic acid (II-9). This compound is shown in Table 1 as compound 3.

Preparation of thiophene analogues of 10deazaaminopterins is illustrated in Reaction Scheme 3.

Starting compounds III-1 and III-2, namely 5-methylthiophene-2-carboxylic acid and methyl 5-methylthiophene-2-carboxylate, are commercially available from Sigma, St Louis, Mo. 5-Bromomethyl-2-carbomethoxythiophene (III-3) is prepared from 5-methylthiophene-2-carboxylic acid by the method described in *Tetrahedron*, 23:2443–51 (1967).

A mixture of III-3, sodium cyanide, benzyltrimethylammonium chloride, dichloromethane, and water is stirred rapidly for about 16 hours. The mixture is then separated. The organic layer is treated with water, then with sodium cyanide, then with benzyltrimethylamonium chloride. This mixture is again rapidly stirred for about 24 hours. The organic layer is removed, dried over magnesium sulfate, and concentrated to give the product 5-cyanomethyl-2-carbomethoxythiophene (III-4).

A solution of III-4 and water in methanol is treated dropwise with a strong acid, such as sulfuric acid. This solution is stirred under argon at about 65° C. for 2–6, preferably for 4 days. The solution is poured onto ice water and extracted with ether twice. The organic extracts are combined and washed with water, saturated sodium bicarbonate then water again, dried over magnesium sulfate and concentrated to afford 2-carbomethoxythiophene-5-acetic acid methyl ester (III-5a).

A suspension of sodium hydride in dry dimethyl formamide is cooled to about 0° C. A solution of the diester (III-5a) in dry dimethyl formamide is added dropwise. The resulting mixture is stirred at about 0° C. for 15–90 minutes, preferably for about 1 hour, then cooled to about −30° C. and treated with a solution of 2,4-diamino-6-bromomethyl pteridine hydrobromide dissolved in dry dimethyl formamide. The resulting mixture is stirred for about 2.5 hours while rising to room temperature, then neutralized to about pH 8 by adding solid carbon dioxide. The mixture is concentrated under high vacuum, and the residue is washed and dried under high vacuum to give the product beta-(2,4-diaminopyrimido [4,5-B]pyrazin-6-yl)-alpha-carbomethoxy-5-ethyl-2-carbomethoxythiophene (III-6a).

A solution of the diester (III-6a) dissolved in an alcohol, such as 2-methoxy ethanol, water, and sodium hydroxide is stirred for about 1.5 hours. The mixture is filtered, and the filtrate is neutralized to about pH 7 with acetic acid and concentrated under high vacuum. The residue is suspended in water, and adjusted with acetic acid to about pH 5 to yield beta-(2,4-diaminopyrimido [4,5-B] pyrazin-6-yl)-alpha-carboxy-5-ethylthiophene-2-carboxylic Acid (III-7a).

A solution of the dicarboxylic acid (III-7a) in argon purged dimethylsulfoxide is placed in a 135° C. oil bath for about 45 min. The solution is then concentrated under high vacuum to a residue that is digested in ether which gives product beta-(2,4-diaminopyrimido[4,5-

B]pyrazin-6-yl)-5-ethylthiophene-2-carboxylic acid (III-Sa).

A solution of the carboxylic acid (III-Sa) in dry dimethyl formamide is treated with triethyl amine and stirred at room temperature for about 1.25 hours. Isobutyl chloroformate is added, and the mixture is stirred for about 1 hour. L-Glutamic acid diethyl ester hydrochloride is added, and the mixture is stirred at room temperature for about 2 hours. Isobutyl chloroformate is then added, and the mixture is stirred for about 1 hour. The process is repeated several times. Concentration of the solution under high vacuum gave beta-(2,4-Diaminopyridimido[4,5-B]pyrazin-6-y)]-5-ethyl-2-thenoyl-glutamic acid diethyl ester (III-9a).

A mixture of the diester (III-9a) in an alcohol such as 2-methoxyethanol is treated with water and 10% sodium hydroxide. The mixture is stirred for about 1 hour, then adjusted to about pH 5.5 with 2-N hydrochloric acid and concentrated under high vacuum. The residue is digested in water and the mixture is filtered. The resulting solid is washed with water and dried to give beta-(2,4diaminopyrimidino[4,5-B]pyrazin-6-yl)-5-ethylthiophen-2-carboxyl-glutamic acid (III-10a). This compound is shown in Table 1 as compound 5.

II. 10-Alkenyl and 10-Alkynyl-10-Deazaaminopterins

In accordance with the present invention, 10-alkenyl and 10-alkynyl 10-deazaminopterin compounds II are provided having the formula:

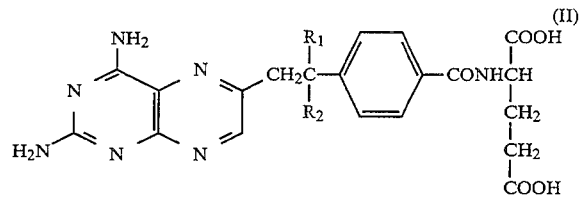

wherein $R_1$ and $R_2$ are selected from the group consisting of hydrogen, alkynyl and alkenyl having from one to about eight, preferably three to five carbon atoms with proviso that when one $R_1$ or $R_2$ is hydrogen then the other must be alkenyl or alkynyl.

Exemplary $R_1$ and $R_2$ alkenyl substituent includes allyl, crotyl (2-butenyl), 2-pentenyl, 4-pentenyl, 2-hexenyl, 5-hexenyl, 3-isopropenyl, 3-isobutenyl, and 2-octenyl.

Exemplary $R_1$ and $R_2$ alkynyl substituent includes propargyl, 2-butynyl, 3-butynyl, 2-pentynyl, 2-hexynyl, and 2-octynyl.

Process for preparing 10-alkenyl and 10-alkynyl 10-deazaminopterin compounds is illustrated in the Reaction Scheme 4.

Reaction Scheme 4

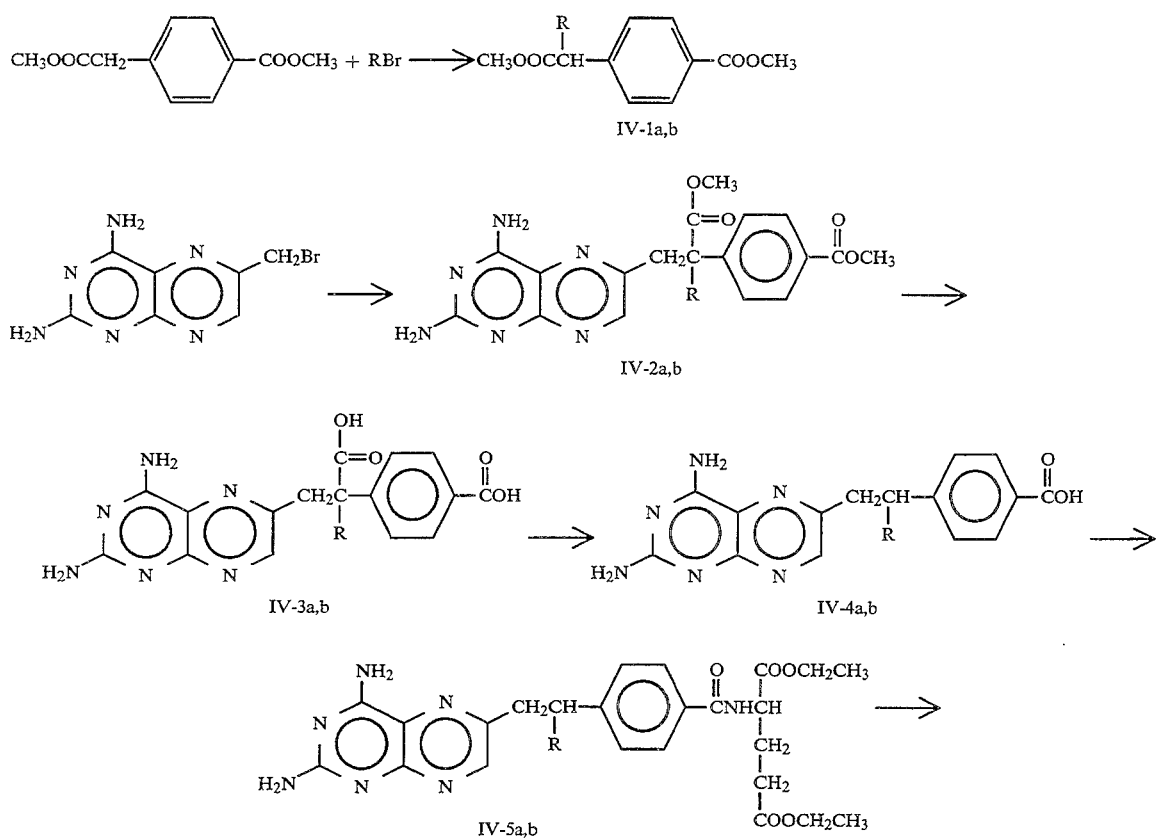

-continued
Reaction Scheme 4

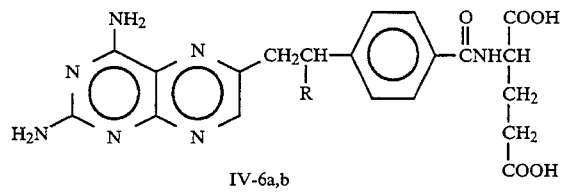

IV-6a,b

Note
Series a) R=CH₂=CHCH₂— in Example 6
b) R—CH≡C—CH₂— in Example 7

Reaction Scheme 4 illustrates preparation of 10-alkenyl or 10-alkynyl deazaaminopterins Step 1 is essentially an alkenylation or alkynylation of the homoterephthalic acid dimethyl ester by the corresponding alkyl, alkenyl or alkynyl bromide.

The reaction proceeds in the presence of an alkali metal hydride and is preferably carried out under anhydrous conditions at low temperatures, well below room temperature, and long reaction times in the presence of an inert polar solvent such as tetrahydrofuran. For example, the alkali metal hydride and solvent are mixed at 0° C., the homoterephthalic acid ester is added, and then the alkyl, alkenyl or alkynyl bromide, again at room temperature or below. The solvent can then be removed, and the reaction product worked up.

In Step 2 of the synthesis, the 2,4-diaminopteridine group is added to the 10-alkyl, alkenyl or alkynyl carbon atom of the homoterephthalic acid ester, again under anhydrous conditions in the presence of alkali metal hydride and a polar solvent, such as dimethyl formamide at low temperatures. The alkali metal hydride is mixed with the inert solvent at a low temperature, well below room temperature, and then a solution of an alpha-alkenyl of alpha-alkynyl homoterephthalic acid ester in the inert solvent is added.

Then the 2, 4-diamino-6-bromo methylpteridine is added slowly, while maintaining the low reaction temperature. After neutralization to about pH 7, the product is worked up.

The resulting 10-alkyl, 10-alkenyl or 10-alkynyl-10-carbomethoxy -4-deoxy-4-amino-10-deazapteroic acid methyl ester is then hydrolyzed to the corresponding 10-carboxy-10-deazapteroic acid in Step 3 with aqueous alkali such as sodium hydroxide, again at low temperature. The reaction mixture is then acidified and worked up.

The 10-carboxy-10-deazapteroic acid from Step 3 is readily decarboxylated in Step 4 by heating a solution in dimethyl sulfoxide at temperatures from 100° to about 160° C. Temperatures of 120°-140° C. were found to be optimal in most cases. Nearly quantitative yields of essentially pure, pale yellow product are routinely obtained. Solvents other than dimethyl sulfoxide may also be used in Step 4.

The resulting 4-amino-4-deoxy-10-deazapteroic acid is then converted to the 10-deazaminopterin compound in two steps. First, the product is reacted with diethyl-L-glutamate, converting the pteroic acid group to the corresponding glutamate, diethyl ester, and the esterifying ethyl groups are then hydrolyzed by reaction with dilute aqueous alkali, such as aqueous sodium hydroxide, forming the free glutamic diacid group of the 10-deazaminopterin compound.

The Step 5 reaction requires an acid acceptor to take up the liberated hydrogen chloride. The Step 5 reaction may be conducted with other alkyl chloroformates such as methyl, ethyl, etc. Acid acceptors are preferably organic bases such as tertiary amines or substituted pyridines, for example, triethylamine, tributylamine, N-methylmorpholine, collidine and lutidine. The diethyl glutamate may be added as the free base or as the hydrochloride salt in the presence of an additional equivalent of the acid acceptor.

The reaction proceeds at room temperature or below, and an inert solvent can be used. The isobutyl chloroformate can be added slowly to the reaction mixture, and upon completion of the reaction, diethyl-L-glutamate, organic amine and more solvent can be added, and reaction continued at the same temperature until complete.

The reaction mixture is worked up by removing the solvent by evaporation, preferably in vacuo, and stirring the residue with a mildly alkaline aqueous solution, such as aqueous sodium bicarbonate. The diester is insoluble, and can be recovered by filtration, while unreacted pteroic acid dissolves in the alkaline solution.

Hydrolysis of the esterifying ethyl groups in Step 6 is carried out with aqueous alkali at room temperature. The diester can be dissolved in a suitable solvent, such as 2-methoxyethanol, and held in the presence of the aqueous alkali until hydrolysis is complete. The acidic 10-deazaminopterin compound is soluble in aqueous alkali, and can then be precipitated by addition of acid, such as glacial acetic acid. The precipitate can be recovered, washed and dried. The diester is readily hydrolyzed to the target compound, such as for example 10-propargyl-10-deazaaminopterin compound IV-6b.

Using the above procedure, with decarboxylation of a 10-carboxypteroic acid intermediate, the following deazaminopterin analogues have been prepared: 10-allyl-10-deazaaminopterin; 10-propargyl-10-deazaaminopterin; 10-propyl-10-deazaaminopterin; 10-allyl-8, 10dideazaaminopterin; 10-propyl-8, 10-dideazaaminopterin; 8, 10-dideazaaminopterin; 5, 10-dideazaaminopterin; 5-CH₃-5, 10dideazaaminopterin; 5-CH₃-10-C₂H₅-5, 10-dideazaaminopterin.

Compound IV-6b was tested in murine leukemia cells test and also for its inhibitory effect on the growth of the mammalian tumor.

Pharmaceutical Compositions

Compounds of the current invention are useful in the method of treatment of rheumatoid arthritis and as active neoplastic agents.

The 10-deazaaminopterin compound of the current invention can be administered per se, or in association with a pharmaceutically acceptable diluent or carrier. The invention accordingly also provides a pharmaceutical composition in dosage unit form comprising from 0.1 to about 500 mg of 10-deazaminopterin compound, per dosage unit, together with a pharmaceutically acceptable nontoxic inert excipient, carrier or diluent.

The 10-deazaaminopterin compound can be formulated in the form of an acid addition salt. These salts are formed with one or more free NH2 groups of the heteroaroyl-10-deazaaminopterin molecule. Typically, the compounds are injected in the form of their sodium salts in aqueous solution. Other salts, such as K, Ca, NH$_4$, and the like, could be used as prepared from the appropriate hydroxide or carbonates.

The acid addition salts are the pharmaceutically acceptable, nontoxic addition salts with suitable acids, such as those with inorganic acids, for example, hydrochloric, hydrobromic, nitric, sulphuric, and phosphoric acids, and with organic acids, such as organic carboxylic acids, for example, glycolic, maleic, hydroxymaleic, malic, tartaric, citric, salicylic, acetyloxybenzoic, nicotinic, and isonicotinic acid, and organic sulphonic acids, for example, methanesulphonic, ethanesulphonic, 2-hydroxyethanesulphonic, toluene-psulphonic, and naphthalene-2-sulphonic acid.

An acid addition salt can be converted into the free compound according to known methods, for example, by treating it with a base, such as with a metal hydroxide or alkoxide, for example, an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example, sodium, potassium or calcium carbonate or hydrogen carbonate, with ammonia; or with a hydroxyl ion exchange resin, or with any other suitable reagent.

An acid addition salt may also be converted into another acid addition salt according to known methods, for example, a salt with an inorganic acid may be treated with a metal salt, for example a sodium, barium or silver salt, of an acid in a suitable diluent, in which a resulting inorganic salt is insoluble and is thus removed from the reaction medium. An acid-addition salt may also be converted into another acid addition salt by treatment with an anion exchange preparation.

The glutamic acid COOH groups can also be in salt form, as the ammonium NH$_4$, alkali metal salts (Na+, K+), or the nontoxic alkaline earth metal salts (Ca++) of the glutamate COOH groups.

The 10-deazaaminopterin compound or salt thereof can be administered to the mammal, including human, by any available route, including oral and parenteral (intravenous, intraperitoneal, subcutaneous, and intramuscular) administration. The amount administered is sufficient to ameliorate the arthritis or other proliferative disease, and will depend upon the type of arthritis, the species of animal, and the weight of the animal. For example, in human administration, a dosage of 10-deazaaminopterin compound within the range from about 0.1 mg/kg to about 500 mg/kg per day should be sufficient. Dosages exceeding the higher part of the range are normally administered in conjunction with leucovorin, 5-formyl tetrahydrofolate, to reduce toxicity. The upper limit of dosage is that imposed by toxic side effects, and can be determined by trial and error for the animal to be treated, including humans.

To facilitate administration, the 10-deazaaminopterin compound or salt thereof can be provided in composition form, and preferably in dosage unit form. While the compound can be administered per se, it is normally administered in conjunction with a pharmaceutically acceptable carrier therefor, which dilutes the compound and facilitates handling. The term "pharmaceutically acceptable" means that the carrier (as well as the resulting composition) is sterile and nontoxic.

The carrier or diluent can be solid, semisolid, or liquid, and can serve as a vehicle, excipient, or medium for the heteroaroyl-10-deazaaminopterin compound. Exemplary diluents and carriers include lactose, dextrose, sucrose, sorbitol, mannitol, starches, gun acacia, calcium phosphate, mineral oil, cocoa butter, oil of theobroma, alginates, tragacanth, propylhydroxybenzoate, talc, or magnesium stearate.

For convenience in handling, the 10-deazaaminopterin compound and carrier or diluent can be enclosed or encapsulated in a capsule, sachet, cachet, gelatin, paper or other container, especially when intended for use in dosage units. The dosage units can for example take the form of tablets, capsules, suppositories, or cachets.

UTILITY

Compounds of the current invention are useful for treatment and prevention of arthritis, particularly rheumatoid arthritis, for suppression of neoplastic growth in tumors, such as mammary tumors, and for suppression of neoplastic growth of blood forming tissues, particularly for treatment of leukemia.

The biological activity of the compounds of the current invention was tested in vitro in culture cells and in vivo in mammals.

The antiarthritic efficacy evaluation used a mouse model of inflammatory disease that occurs in response to an antigenic challenge with Type II collagen according to method described in *Nature*, 283,666–668 (1980).

The fundamental aspects of the mouse model allow it to serve as a representative presentation of human disease. The parallels between the known aspects of the mouse model and rheumatoid arthritis include a humoral response in which antibodies are produced to an antigen that is present in the joint tissue and the antigenic challenge is accompanied by cell-mediated aspects of immunity. The resultant inflammation of the joint tissue yields facets of periostitis, synovial lining hyperplasia, degradation of bone and cartilage and pannus and new bone formation.

Antineoplastic activity of the compounds of the current invention was tested by the effect of 10-propargyl-10-deazaaminopterin on growth inhibition of L 1210 murine leukemia cells in culture and for its ability to inhibit dihydrofolate reductase derived from L 1210 cells.

The used method was according to *Biochem. Pharmacol.*, 28:2993–2997 (1973). Enzyme was derived from L 1210 murine leukemia cells. The inhibition was conducted at pH 7.3. Data were analyzed according to method described in *Biochem J.*, 135:101–107 (1973). Methotrexate was used as a control.

In vivo effect of 10-propargyl-10-deazaaminopterin in suppression of the tumor growth was evaluated in the EO771 murine mammary tumor model according to method described in *Proc. Ann. Soc. Clin. Oncol.*, 11:51 (1992).

Tumor evaluation was performed in EO771 solid subcutaneous mammary tumor in BDF1 female mice. The mice were injected with tested compound with doses as indicated in Table 6. Results are described in Example 16. Methotrexate was not as effective in this assay. The EO771 solid tumor model is predictive for activity in human breast cancer as demonstrated by 10-ethyl-10-deazaminopterin (Edatrexate).

The following Examples are intended to illustrate the preparation of representative compounds, methods and procedures of this invention. They are not to be interpreted to limit the scope of this invention in any way.

EXAMPLE 1

N-[Beta-(2,4-Diaminopyrimido-[4,5-B-]-pyrazin-6-yl)-6 ethylnicotinoy] glutamic Acid (I-7a).

This example illustrates a preparation of N-[beta(2,4-diaminopyrimido-[4,5-B-]-pyrazin-6-yl)-6-ethylnicotinoyl-] glutamic Acid (I-7a) according to the procedure illustrated in the Reaction Scheme 1. The compound is listed in the Table 1 as compound 3.

5-Carbomethoxy-2-pyridylacetic Acid Methyl Ester (I,!).

Freshly distilled diisopropylamine (7.4 g, 73 mmol) in dry tetrahydrofuran (100 mL) was cooled under argon to 0° C., then treated dropwise with n-butyl lithium in hexane (50 mL of a 1.6-M solution) and stirred at 0° C. for 1 hour. The lithium diisopropyl amide solution was added dropwise over 45 minutes to a −25° C. mixture of 6-methylnicotinic acid (4.0 g., 29 mmol) and hexamethylphosphorous triamide (5.23 g) in dry tetrahydrofuran. The solution became red. The temperature of the red solution was allowed to rise to 0° C. whereupon stirring was continued for 2 hours. Carbon dioxide was bubbled through the 0° C. solution, resulting in a yellow precipitate. The mixture was allowed to rise to room temperature and was stirred for 16 hours. Filtration gave a yellow solid that was suspended in methanol (50 mL) and the mixture was cooled to 0° C. Saturated methanolic HCl was added, and the solution was stirred at room temperature for 72 hours. Concentration in vacuo gave a residue that was partitioned between ether and saturated sodium bicarbonate. The ether layer was washed with water, dried over magnesium sulfate, and concentrated to an orange oil. Chromatography on flash silica gel (5% ethyl acetate in hexanes) gave the product I-la as a yellow solid yielding 1.84 g (30%). M.p. 56°–57°.

Analysis gave the following results. NMR (CDCl3): delta 9.10 (m, 1H, 6-H); 8.21 (m, 1H, 4-H); 7.33 (m, 1H, 3H) 3.84 (m, 8H, $CH_2COOCH_3 + ArCOOCH_3$). Anal. Calcd. for $C_{10}H_{11}NO_4$: C, 57.41%; H, 5.30%; N, 6.70%. Found: C, 57.53%; H, 5.33%; N, 6.54%.

Alpha-ethyl-5-carbomethoxy-2-pyridylacetic Acid Methyl Ester (I-2)

A 0° C. suspension of sodium hydride (1.14 g, 50% in oil, 0.57g of sodium hydride, 23.8 mmol) in dry dimethyl formamide was treated dropwise with a solution of I-I (4.98 g, 23.8 mmol) in dry dimethyl formamide (15 mL). This mixture was stirred at 0° C. for 1 hour, then cooled to 30° C. A solution of ethyl iodide (3.72 g, 23.8 mmol) in dry dimethyl formamide (50 mL) was added dropwise, maintaining a −25° C. reaction temperature, then stirred for 2 hours at room temperature. The reaction was neutralized to pH 8 by adding solid carbon dioxide, then concentrated under high vacuum. The residue was partitioned between ether and water. The organic layer was washed with 10% sodium bicarbonate, 10% sodium bisulfite, and water. The organic layer was dried over magnesium sulfate and concentrated to a pale brown oil. Chromatography on flash silica gel (5% ethyl acetate in hexane) gave the product I-2 as a yellow oil (2.86 g, 51%) that was pure by TLC (10% ethyl acetate in hexanes on silica gel). Analysis gave the following results.

NMR (CDCl3) delta 9.13 (m, 1H, 6-H); 8.26 (m, 1H, 4-H); 7.39 (m, 1H, 3-H); 3.83 (m, 7H, 2 X $OCH_3$+alpha-CH); 2.10 (m, 2H, $CH_2CH_3$); 0.87 (t, 3H, $CH_3CH_2$). Anal. Calcd. for $C_{12}H_{15}NO_4$: C, 60.75%; H, 6.37; N, 5.90. Found: C, 60.63%; H, 6.38%; N, 5.89%.

3-(2,4-Diaminopyrimido[4,5-B]pyrazin-6-yl)-2-(3-carbomethoxypyrid-6-yl)-propionic Acid Methyl Ester (I-3a)

To a 0° C. suspension of sodium hydride (0.69 g of 50% sodium hydride in oil, 14.3 mmol) in dry dimethyl formamide (10 mL) was added dropwise a solution of I-2 (3.0 g, 14.3 mmol) in dry dimethyl formamide (10 mL). The mixture was stirred at 0° C. for 30 minutes, then cooled to −30° C. A solution of 2,4 diamino-6-bromomethylpteridine hydrobromide (4.8 mmol) in dry dimethyl formamide (30 mL) was added dropwise over 40 minutes. The reaction was stirred for 2.5 hours at 10° C., then adjusted to pH 8 by adding dry ice. Concentration under high vacuum gave a residue that was washed with ether, then water. Drying in vacuo at room temperature gave the product I-3a as a yellow solid, 1.8 g (99%).

Anal. Calcd. for $C_{17}H_{17}N_7O_4$. 17 $H_2O$: C, 49 32%; H, 4.96%; N, 23.68%. Found: C, 49.56%; H, 4.21; N, 23.25%.

Beta-(2,4-Diamino-[4,5-B]pyrazin-6-yl)-6-ethylnicotinic Acid (I-5a)

A solution of the diester I-3a (1.8 g, 4.7 mmol) in 2-methoxyethanol (20 mL), water (20 mL), and 10% sodium hydroxide (20 mL) was stirred for 2.5 hours, then diluted with water (40 mL). The reaction was adjusted to pH 6 with glacial acetic acid. The cream-colored precipitate was collected, washed with water, and dried to yield 1.61 g (58%) of product I-4a. HPLC indicated 95.3% purity.

A mixture of the dicarboxylic acid I-4a (0.5 g, 1.4 mmol) in dry argon-purged dimethyl sulfoxide (40 mL) was heated to 110° C. for 25 minutes, then concentrated under high vacuum. The residue was suspended in water (40 mL), and sufficient ammonium hydroxide was added to produce a solution. The solution was adjusted to Ph 5 by dropwise addition of glacial acetic acid, then the precipitate was collected. The resulting yellow solid was washed with water and dried to yield 0.4 g (94%) of product I-5a.

HPLC shows 92% purity. Analysis gave the following results. Mass spectrum m/e 527 (TMS3). Anal. Calcd. for $C_{14}H_{13}N_2O_2$ . 2.0 $H_2O$: C, 48.41%; H, 4.93; N, 28.23. Found: C, 48.95; H, 4.89; N, 27.79.

N-[Beta-(2,4-Diaminopyrimido-[4,5-B]-pyrazin-6-yl)-6ethylnicotinoyl]-glutamic Acid Diethyl Ester (I-6a)

A mixture of the carboxylic acid I-5a (0.4 g, 1.25 mmol) in dry dimethyl formamide was treated with triethyl amine (1.2 g, 11.8 mmol). After being stirred for 1 hour, the mixture was treated with isobutyl chloroformate (0.35 g, 2.6 mmol). The mixture was stirred for 1 hour at room temperature and treated with L-glutamic acid diethyl ester hydrochloride (0.62 g, 2.6 mmol). After 2 hours, the mixture was treated with isobutyl chloroformate (0.18 g, 1.3 mmol). The mixture was stirred for 1 hour and treated with L-glutamic acid diethyl ester hydrochloride (0.31 g, 1.3 mmol). After 1 hour of stirring, isobutyl chloroformate (0.18 g, 1.3 mmol) was added. The mixture was stirred for additional 1 hour. L-glutamic acid diethyl ester hydrochloride (0.31 g, 1.3 mmol) was added, and the mixture was stirred for 16 hours. The mixture was concentrated under high vacuum. The residue was washed thoroughly with ether, then with water. The residue was crystallized from hot ethanol, giving yellow crystals (0.31 g, 50% theory) of product I-6a. Analysis gave the following results.

TLC (20% methanol in chloroform on silica gel plates) Rf=0.2; mass spectrum m/e 497 (M+H). Anal. Calcd. for $C_{23}H_{28}N_8O_5 \cdot H_2O$: C, 53.68%; H, 5.87%; N, 21.77%. Found: C, 53.45%; H, 5.70%; N, 21.78%. NMR (d6DMSO) delta 8.90 (d, 1H, NHCO); 8.87 (d, 1H, pyr 6'-H), 8.61 (s, 1H, Cv-H); 8.10 (m 1H, pyr 4'-H); 7.70 (broad d. 1H, NH); 7.42 (d, 1H, pyr 3'-H); 6.65 (broad s, 2H, NH2); 4.40 (m, 1H, CHN); 4.05 (m, 4H, 2 X OCH2); 3.30 ($CH_2CH_2 + H_2O$); 2.45 (t, 2H, $CH_2CO_2$); 2.05 (m, 2H, CH2CH); 1.70 (t, 6H, 2 X CH3).

N-[Beta-(2,4-diaminopyrimido-[4-5-$\beta$-]-pyrazin-6-yl)-6-ethylnicotinoyl-] glutamic Acid CI-7a) (Compound No. 1)

Diester I-6a (0.3 g, 0.6 mmol) was dissolved in 2-methoxyethanol (10 mL), 10% sodium hydroxide (5 mL) and water (4 mL) and stirred at room temperature for 2.5 hours. The solution was then diluted with water (20 mL), adjusted to pH 6 with acetic acid, and filtered. The resulting yellow solid was washed with water and dried to give the product I-7a as a fine powder (0.19 g, 71%). HPLC (see above conditions) shows 95% purity. Analysis gave the following results.

Mass spectrum m/e 729 ($TMS_4M+H$); UV (0.1N NaOH) 258 nm (25,000) 275 sh (13, 900), 371 (6,600). Anal. Calcd. for $C_{19}H_{20}N_8O_5$, 2,25 H20: C, 47.44%; H, 5.14%, N, 23.30%. Found: C, 47 04%; H, 4 64%; N 23.64%.

EXAMPLE 2

N-[Alpha-Ethyl-beta-(2,4-diaminopyrimido-[4,5-$\beta$]-pyrazin-6-yl)-6-ethylnicotinoyl]-glutamic Acid (I-7b)

This example illustrates a preparation of N-[alpha-ethyl-beta-(2,4-diaminopyrimido-[4,5-$\beta$]-pyrazin-6-yl)-6-ethylnicotinoyl]-glutamic acid (I-7b) according to procedure illustrated in the Reaction Scheme 1. Example yields compound 2, listed in Table 1.

3-(2,4-Diaminopyrimido[4,5-$\beta$]-pyrazin-6-yl)-2-(3-carbomethoxypyrid-6-yl) -2-ethylpropionic Acid Methyl Ester (I-3b)

A 0° C. suspension of sodium hydride (0.56 g, 50% in oil, 11.8 mmol of sodium hydride) in dry dimethyl formamid, (10 mL) was treated dropwise with a solution of the diester I-2 (2.8 g, 11.8 mmol) in dry dimethylformamide (10 mL). The resulting mixture was stirred at 0° C. for 1 hour, then cooled to −30° C. A solution of 2,4-diamino-6-bromomethylpteridine hydrobromide (3.9 mmol) in dry dimethyl formamide was added, maintaining a −25° C. internal temperature. The reaction mixture was allowed to stir for 2 hours as it rose to room temperature. The mixture was adjusted to pH 8 by adding solid carbondioxide. Concentration under high vacuum gave a residue that was washed with ether, then water. The resulting yellow solid was dried in vacuo, giving 1.26 g (78%) of product I-3b. Analysis gave the following results.

Mass spectrum m/e 412 (M+H). NMR (d6DMSO) delta 9.04 (s, 1H, C7-H); 8.23 (m, 2H, pyr 5'-H+pyr 4'-H); 7.45 (d, 1H, pyr 2'-H) ;6.62 (broad s, 2H, NH2); 3.87 (s, 3H, ArCOOCH3); 3.62 (m, 5H, $C_{10}COOCH_3 + C_9-H_2$); 2.01 (m, 2H, CH2CH3); 0.80 (t, 3H, CH3CH2). Anal Calcd. for $C_{19}H_{21}N_7O_4 \cdot 1.5 H_2O$: C, 52.04%; H, 5.51%; N, 22.36%. Found: C, 52.22%; H, 5.18%; N, 22.49%.

3-(2,4-diaminopyrimido[4,5,$\beta$]pyrazin-6-yl),2(3-carboxypyrid-6-yl)-2-ethylpropionic Acid (I-4b)

A solution of the diester I-3b (1.24 g, 3.0 mmol) in 2-methoxyethanol (20 mL), water (20 mL), and 10% sodium hydroxide (20 mL) was stirred for 15 hours. The reaction was adjusted to pH 7 with glacial acetic acid, then concentrated under high vacuum. The residue was treated with water (10 mL) and adjusted to pH 4 with 4N hydrochloric acid, and the precipitate was collected. The resulting tan solid washed with water and dried in vacuo yielded 0.31 g (27%) of product I-4b.

Alpha-ethyl-beta-(2,4-diaminopyrimido-[4,5-b]-pyrazin-6 yl)-6-ethyl nicotinic Acid (I-5b)

The dicarboxylic acid I-4b (0.31 g) was dissolved in dry dimethyl formamide (8 mL). The solution was allowed to stand at room temperature for 20 minutes. Concentration under high vacuum gave a residue that was washed with ether. The resulting tan solid was dried in vacuo to give the product I-5b in 99% yield. HPLC showed the product to be of 90% purity.

N-[Alpha-ethyl-beta-(2,4-diaminopyrimido-[4,5-beta]-pyrazin-6-yl)-6-ethyl-nicotinoyl]-glutamic Acid Diethyl ESter (I-6b)

A mixture of the carboxylic acid I-5b (0.31 g, 0.75 mmol) and triethylamine (0.73 g, 7.2 mmol) in dry dimethyl formamide (20 mL) was stirred at room temperature for 15 minutes. Isobutyl chloroformate (0.22 g, 1.6 mmol ) was then added, and the mixture was stirred for 1 hour. L-Glutamic acid diethyl ester hydrochloride (0.38 g, 1.6 mmol) was added, and the mixture was stirred for 2 hours. Isobutyl chloroformate (0.11 g, 0.8 mmol) was added, and the mixture was stirred for 1 hour. L-Glutamic acid diethyl ester hydrochloride (0.19 g, 0.8 mmol) was added, and the mixture was stirred at room temperature for 1 hour. Isobutyl chloroformate (0.11 g, 0.8 mmol) was added, and the mixture was stirred for 1 hour. L-Glutamic acid diethyl ester hydrochloride (0.19 g., 0.8 mmol) was added, and the mixture was stirred for additional 16 hours. The mixture was filtered and the filtrate concentrated under high vacuum. The residue was chromatographed on flash silica gel (5% methanol in chloroform eluent), giving the product I-6b as an orange glass (0.23 g, 48%). Analysis gave the following results.

Mass spectrum m/e 525 (M+H) ; NMR (CDCl3) delta 9.01 (broad s, 1H, pyr 6'-H; 8.45 (broad s, 1H, 7-H); 7.97 (d, 1H, pyr 4'-H); 7.35 (broad s, 2H, NH2); 7.08 (d, 1H, pyr 3'-H); 5.38 (broad s, 2H, NH2); 4.75 (m, 1H, CHN): 4.19 (m, 4H, 2 X OCH2); 3.32 (m, 3H, $C_9$-$H_2 + C_{10}$-H); 2.50 (m, 2H, $C_{10}$-$CH_{26l}$); 2.23 (m, 4H, glu $C_4$-$H_2$ + glu $C_3$-$H_2$); 1.26 (m, (6H, 2 X OCH2CH3); 0.83 (t, 3H, $C_{10}$-CH2CH3)/

N-[Alpha-ethyl-beta-(2,4,-diaminopyrimido-[4,5-beta]-pyrazin-6-yl)-6-ethylnicotinoyl]-glutamic Acid (I-7b, Compound No. 2 )

The diester I-6b (0.2g, 0.38 mmol ) was dissolved in 2-methoxyethanol (6 mL) and 10% sodium hydroxide (1.6 mL) and stirred for 1 hour at room temperature. The solution was adjusted to pH 7 with acetic acid and concentrated under high vacuum. The residue was dissolved in water (7 mL) and acidified to pH 3 with 4M hydrochloric acid, then filtered. The resulting tan solid was washed with water and dried in vacuo to yield 70 mg (39%) of product I-7b. HPLC (see above conditions) showed 98.9% purity. Analysis gave the following results.

Mass spectrum m/e 757 (TMS4), (M+H) ; UV (0.1N NaOH) 256 nm (25,246) 367 (6562). Anal. Calcd. for $C_{21}H_{24}N_8O_5 \cdot 1.4 H_2O$: C, 51.09%; H, 5.47%; N, 22.68%. Found: C, 51.12%; H, 5.29%; N, 22.55%.

EXAMPLE 3

Beta-[3-(2,4)-Diaminopyrimido[4,5-$\beta$]-pyrazin-6-yl]-4-ethylpicolinoyl]glutamic Acid This example illustrates a preparation of beta-[3(2,4)-diaminopyrimido[4,5-$\beta$]-pyrazin-6-yl]-4ethyl-picolinoyl]glutamic acid (III-9) according to procedure illustrated in the Reaction Scheme 2. The resulting compound is listed in Table 1 as compound 5.

2-Carbomethoxy-5-pyridylacetic Acid Methyl Ester (II-1)

The diester (II-1) was prepared in a manner similar to that of preparation of compound I-1 from 5-methylpicolinic acid (10.0 g, 73 mmoles) resulting in an amber oil product in 49% yield. Analysis gave the following results.

NMR (CDCl$_3$): delta 8.63 (d, 1H, C$_3$-H); 8.15 (d, 1H, C$_6$-H); 7.81 (m, 1H, C$_4$-H); 4.02 (s, 3H ArCOOCH$_3$); 3.75 (s, 5H, CH$_2$COOCH$_3$).

2-Carbomethoxy-5-pyridylacetic Acid Benzhydryl Ester (11-3)

A solution of potassium hydroxide (1.39 g, 24.8 mmoles) in 90% methanol (100 mL) was treated with a solution of compound II-1 (5.18 g, 24. 8 mmoles) in methanol (14 mL). After 2 hours the solution was adjusted to pH 6.5 by hydrochloric acid addition. The solution was concentrated in vacuo to give a tan solid that was a mixture of both monoesters, the dicarboxylic acid and the starting diester. HPLC indicated the desired monoester (II-2) to represent 57% of the mixture.

The mixture of compound II-2 in chloroform (100 mL) was cooled to 0° C. and treated dropwise with a solution of diphenyldiazomethane (5.27 g, 27.2 mmoles) in chloroform (50 mL). The resulting purple mixture was stirred at ambient temperature for 24 hours. The solution was washed with saturated sodium bicarbonate and water. The organic layer was dried over magnesium sulfate and concentrated to a purple syrup. Crystallization from pentane gave the product II-3 as a white solid, 1.86 g (21% yield from II-1). Analysis gave the following results.

NMR (CDCl$_{13}$): delta 8.68 (m, 1H, C3-H); 8.10 (d, 1H C6-H); 7.75 (m, 1H, C$_4$-H); 7.30 (m, 10H, 2 x C$_6$H$_5$); 6.90 (s, 1H, OCH); 4.05 (s, 3H, OCH$_3$); 3.81 (s, 2H, CH$_2$). Anal. Calcd. for $C_{22}H_{19}NO_4 \cdot 0.25 H_2O$: C, 72.21; H, 5.37; N, 3.83. Found C, 72.43; H, 5.49; N, 3.69. TLC (40% ethyl acetate in hexanes on silica gel) showed a single spot at Rf 0.5.

3-(2,4-Diaminopyrimido[4,5-$\beta$-pyrazin-6-yl)-2-(2-carbomethoxypyrid-5-yl)propionic Acid Benzhydryl Ester (II-4)

A 0° C. suspension of sodium hydride (413 mg of 50% in oil, 8.6 mmoles) in dry N,N-dimethylformamide (20 mL) was treated dropwise with a solution of compound II-3 (3.11 g, 8.6 mmoles) in dry dimethylformamide (25 mL). The yellow-green mixture was stirred at 0° C. for 2 hours, becoming a red solution. This was cooled to −25° C. and treated, dropwise with a solution of 2,4-diamino-6-bromomethylpteridine hydrobromide (3.4 mmoles) in dry dimethylformamide (20 mL) with maintenance of the temperature at −25° C. The mixture was stirred at 22° C. for 2.5 hours and adjusted to pH 8 by addition of dry ice. Concentration under high vacuum gave a residue which was washed with ether and water. The yellow solid was dried in vacuo and chromatographed on flash silica gel using 4% methanol in chloroform as eluant to yield the product II-4 as a yellow powder 1.33 g (75% yield). Analysis gave the following results.

NMR (CDCl$_3$): delta 8.80 (m, 1H, CT-H); 8.62 (s, 1H, C$_3$'-H); 8.10 (d, 1H, C$_6$'-H); 7.84 (m, 1H, C$_4$'-H); 7.20 (m, 12H, 2 x C$_6$H$_5$+NH$_2$); 6.80 (s, 1H, OCH); 5.20 (broad s, 2H, NH$_2$); 4.55 (m, 1H, C$_{10}$-H); 4.02 (s, 3H, OCH$_3$); 3.85 (m, 1H, C$_9$-H); 3.30 (m, 1H, Cg-H).

beta- (2,4 -Diaminopyrimido[4,5-$\beta$]-pyrazin-6-yl)-4-ethylpicolinic Acid Methyl Ester (II-6)

A mixture of the diester II-4 (1.29 g, 2.4 mmoles) in dichloromethane (67 mL) was treated with 99% trifluoroacetic acid (33 mL). The yellow solution was kept at room temperature for 50 minutes then concentrated at room temperature under high vacuum. The residue was washed repeatedly with ether then dried in vacuo giving a bright yellow solid. This was suspended in water and neutralized to pH 6 with 1.5 M ammonium hydroxide. The mixture was concentrated under high vacuum giving a yellow solid product II-5, 0.99 g. HPLC confirmed the conversion to II-5.

A solution of the monocarboxylic acid, II-5 (0.99 g crude) in 40 mL of dimethylsulfoxide, was stirred at 130° for 30 minutes. HPLC showed disappearance of the starting carboxylic acid (II-5) at retention time 4.4 minutes and the desired monoester to be present (retention time 15.2 minutes). The solution was concentrated under high vacuum and the residue was washed with ether and water. The orange solid was collected and dried in vacuo at room temperature to afford 505 mg (64%) of product II-6.

NMR (CDCl$_3$): delta 8.60 (m, 2H, C$_7$-H, 6'-H); 8.10 (d, 1H, 3'-H); 7.85 (d, 1H, 5'-H); 7.20 (m, 3H, NH$_2$); 4.00 (s, 3H, OCH3); 3.35 (s, 4H, CH$_2$CH$_2$).

Beta-(2,4-diaminopyrimido[4,5-$\beta$]-pyrazin-6-yl)-4-ethyl picolinic Acid (II-7)

A mixture of the ester II-6 (0.49 g, 1.5 mmoles) in 2-methoxyethanol (5 mL) was treated with water (5 mL) then 10% sodium hydride (2.5 mL). After stirring 45 minutes, the resulting red solution showed complete saponification by HPLC.

The solution was neutralized to pH 7.5 with hydrochloric acid and concentrated under high vacuum. The resulting residue was treated with water and stirred.

Filtration gave 0.27 g of product as an orange solid (57%). HPLC showed 96% purity. Mass spectrum m/e 527 (TMS$_3$).

beta-[(2,4)-Diaminopyrimido(4,5-$\beta$)-pyrazin-6-yl)-4-ethylpicolinoyl]glutamic Acid Diethyl Ester (II-8)

A mixture of the carboxylic acid II-7 (0.27 g, 0.87 mmol) and triethylamine (822 mg, 8.12 mmol) in dry dimethyl formamide (15 mL) was stirred at room temperature for 15 minutes. Isobutyl chloroformate (0.23 mL, 1.78 mmole) was added and the mixture was stirred for 1 hour. L-Glutamic acid diethyl ester hydrochloride (427 mg, 1.78 mmol) was added and the mixture was stirred for 2 hours. The addition of isobutyl chloroformate and diethyl glutamate was repeated at one-half the initial quantities and the final mixture was stirred for 16 hours. After filtration, the filtrate was concentrated in vacuo and the residue was partitioned between water and chloroform. Chromatography of the chloroform soluble portion yielded 72 mg (18%) of the diester II-8. Analysis gave the following results.

NMR (CDCl$_3$): delta 8.60 (d, 1H, C$_7$-H); 8.55 (d, 1H, NH); 8.43 (d, 1H, C$_5'$-H);8.06 (d, 1H, C$_2'$-H); 7.70 (m, 1H, C$_6'$-H); 4.80 (m, 1H, CHNH); 4.20 (m, 4H, 2x OCH$_2$); 2.30 (m, 4H, glu CH$_2$CH$_2$); 1.30 (m, 6H, 2x OCHC$_2$CH$_3$). Mass spectrum m/e 496.

Beta-(2,4)-Diaminopyrimido[4,5-$\beta$]-pyrazin-6-yl-4-ethylpicolinoyl]glutamic Acid (II-9, Compound No. 5)

The diester II-8 (67 rag, 0.13 mmol) was dissolved in 2-methoxyethanol (2.3 mL) and 10% sodium hydroxide (2.2 mL) was added. The mixture was stirred for 2 hours at room temperature. The solution was adjusted to pH 5-6 with acetic acid and evaporated in vacuo. The residue was dissolved in 2 mL of water and acidified to pH 3-4. The solid was collected, washed with water, and dried to leave 34 mg (58%) of product II-9.

HPLC shows 99.3% purity. UV (0.1 M NaOH) 257 (22,200); 371 (5,600). Mass spectrum m/e 729 (TMS$_4$).

EXAMPLE 4

Beta-(2,4-Diaminopyrimidino[4,5-$\beta$]pyrazin-6-yl)-5-ethyl-2-thenoyl-glutamic Acid This example illustrates preparation of compound beta(2,4-Diaminopyrimidino[4,5-$\beta$]pyrazin-6-yl)-5-ethyl-2-theonyl-glutamic acid, as seen in Table 1, by the procedure illustrated in Reaction Scheme 3.

5-Methyl-2-Thenoic Acid and Its Methyl Ester (III-1 and III-2)

2-Methyl-2-thenoic acid (III-1) and its methyl ester (III-2) are commercially available and the source can be found, for example in *Chemical Sources U.S.A.* published annually by Directories Publishing, Inc. of Boca Ratan, Fla. or they can be readily prepared by methods known in the art.

5-Bromomethyl-2-carbomethoxythiophene (III-3).

This compound was prepared from 5-methylthiophene-2-carboxylic acid by the method of Gogte et al, *Tetrahedron*, 23, 2443-51 (1967).

5-Cyanomethyl-2-carbomethoxythiophene (III-4)

A mixture of III-3 (18.0 g, 76.6 mmol), sodium cyanide (15.0 g, 0.31 mmol), benzyltrimethylammonium chloride (1.75 g, 9.4 mmol), dichloromethane (75 mL), and water (75 mL) was stirred rapidly for 16 hours. The mixture was then separated. The organic layer was treated first with water (75 mL), then with sodium cyanide (15.0 g, 0.31 mmol), and last with benzyltrimethylamonium chloride (1.5 g, 8.0 mmol). This mixture was again rapidly stirred for 24 hours. The organic layer was removed, dried over magnesium sulfate, and concentrated. The residue was chromatographed on 250 g of flash silica gel using 20% ethyl acetate in hexane as an eluent, to give the product (III-4) as a yellow crystalline solid, 4.53 g (33%). Analysis gave the following results.

NMR (CDCl$_3$) d 7.66 (d, 1H, C$_3$-H); 7.03 (d, 1H, C$_4$-H); 3.83 (d, 5H, CH$_3$+CH$_2$); mass spectrum m/e 196 (M +H); TLC (10% ethyl acetate in hexanes on silica gel plates); R$_f$—0.3.

2-Carbomethoxythiophene-5-acetic Acid Methyl Ester (III-5a)

A solution of compound III-4 (0.5 g, 2.7 mmol) and water (0.2 g) in methanol (7.5 mL) was treated dropwise with concentrated sulfuric acid (1.5 mL). This solution was stirred under argon at 65° C. for four days. The pale yellow solution was poured onto ice-water (50 mL) and extracted with ether (2×50 mL). The organic extracts were combined and washed with water, followed with saturated sodium bicarbonate, then with water again, and dried over magnesium sulfate. The solution was concentrated to a clear, colorless oil that solidified to a white, waxy solid (0.4 g, 68%). Analysis gave the following results.

NMR (CDCl$_3$): delta 7.61 (delta, 1H, 3-H); 6.90 (delta, 1H, 4-H); 3.87 (m, 5H, ArCOOCH$_3$+CH$_2$); 3.82 (s, 3H, CH$_2$COOCH$_3$). TLC (10% ethyl acetate in hexane on silica gel) R$_f$=0.4. Calc. C9 H$_{10}$O$_4$ S; C,50.46; H,4.70. Found: C,50,57; H, 4.79.

$\beta$]-(2,4-Diaminopyrimido[4,5-$\beta$]pyrazin-6-yl)-alphacarbomethoxy-5-ethyl-2-carbomethoxythiophene (III-6a)

A suspension of sodium hydride (0.84 g, 17.5 mmol) in 15 mL of dry dimethyl formamide was cooled to 0° C. A solution of the diester compound III-5a (3.73 g., 17.4 mmol) in 15 mL of dry dimethyl formamide was added dropwise. The resulting mixture was stirred at 0° C. for one hour, then cooled to −30° C. and treated with a solution of 2,4 diamino-6-bromomethylpteridine hydrobromide (16.1 mmol) in 40 mL of dry dimethyl formamide. The resulting mixture was stirred for 2.5 h while rising to room temperature, then neutralized to pH 8 by adding solid carbon dioxide. The mixture was concentrated under high vacuum, and the residue was washed with ether, then water, and dried under high vacuum to give the product III-6a as a yellow solid (1.98 g., 88%). Analysis gave the following results.

Mass spectrum m/e 389 (M +H). NMR (d$_6$DMSO) delta 8.58 (s, 1H$_7$-H); 7.60 (m, 3H, C$_4$-H+NH$_2$); 7.12 (d, 1H, C$_3'$-H); 6.61 (broad s, 2H, NH$_2$); 4.9 (t, 1H, C$_3'$-H); 3.75 (s, 3H, C$_2'$-COOCH$_3$); 3.63 (m, 5H, C$_{10}$-COOCH$_3$+C$_9$-H$_2$).

Beta-(2,4-Diaminopyrimido[4,5,$\beta$]pyrazin-6-yl)-alpha-carboxy-5-ethylthiophene-2-carboxylic Acid (III-7a)

A solution of the diester III-6a (1.96 g, 5.05 mmol) in 30 mL of 2-methoxyethanol, water, and 30 mL of 2.5 M sodium hydroxide was stirred for 1.5 hours. The mixture was filtered, and the filtrate was neutralized to pH 7 with acetic acid and concentrated under high vacuum.

The residue was suspended in water (30 mL) and adjusted with acetic acid to pH 5 to yield a precipitate. Filtration gave a tan solid that was digested in 95% ethanol. Filtration gave a tan solid that was washed with ether and dried in vacuo, yielding 1.31 g (77%) of product III-7a. Analysis gave the following results.

HPLC (Novapak C18 column, 25% methanol in 0.1 molar $NaH_2PO_4$, pH 6.5) indicated 92.2% purity; NMR ($d_6DMSO$) delta 8.51 (s, 1H, $C_7$-H); 7.55 (broad s, 2H, $NH_2$); 7.17 (d, 1H, 4'-H); 6.81 (d, 1H, 3'-H); 6.55 (broad s, 2H, NH2); 4.40 (t, 1H, $C_{10}$-H); 3.15 (m, 2H, $C_9$-$H_2$).

Beta-(2,4-Diaminopyrimido[4,5-β]pyrazin-6-yl)-5-ethylthiophen-2-carboxylic Acid (III-Sa)

A solution of the dicarboxylic acid III-7a (1.31 g, 3.64 mmol) in argon purged dimethylsulfoxide was placed in a 135° C. oil bath for 45 minutes. The solution was then concentrated under high vacuum to a residue that was digested in ether. Filtration yielded a brown solid that was washed with ether and dried in vacuo at room temperature to give 1.31 g of crude product, which was suspended in water (75 mL) and treated dropwise to pH 12 with ammonium hydroxide. The mixture was filtered and the filtrate adjusted to pH 5 with acetic acid. Filtration gave a brown solid that was dried in vacuo, yielding 0.97 g (84%) product III-Sa. Analysis gave the following results.

HPLC indicated 86% purity. Anal. Calcd. for $C_{13}H_{12}N_6O_2S \cdot H_2O$: C, 46.69%; H, 4.22%; N, 25.13%. Found: C, 46.80%; H, 4.01%; N, 24.82%.

Beta-(2,4-Diaminopyridimido[4,5-b]pyrazin-6-y1)-5-ethyl-2 Thenoyl-glutamic Acid Diethyl Ester (III-9a)

A solution of the carboxylic acid III-Sa (0.7 g, 2.2 mmol) in dry dimethyl formamide (40 mL) was treated with triethylamine (2.1 g, 21.0 mmol) and stirred at room temperature for 1.25 hours. Isobutyl chloroformate (0.63 g, 4.6 mmol) was added, and the mixture was stirred for 1 hour. L-Glutamic acid diethyl ester hydrochloride (1.1 g, 4.6 mmol) was added, and the mixture was stirred at room temperature for two hours. Isobutyl chloroformate (0.32 g, 2.3 mmol) was then added, and the mixture was stirred for one hour. L-glutamic acid diethyl ester hydrochloride (0.55 g, 2.3 mmol) was added, and the mixture was stirred for one hour. Isobutyl chloroformate (3.2 g, 2.3 mmol) was added, and the mixture was stirred at room temperature for one hour. L-Glutamic acid diethyl ester hydrochloride (0.55 g, 2.3 mmol) was added, and the mixture was stirred at room temperature overnight. Concentration under high vacuum gave a dark residue that was washed repeatedly with ether. The residue was then washed with dilute ammonium hydroxide, then water. The resultant orange solid was dried in vacuo. Chromatography on flash silica gel (2.5% methanol in chloroform) gave the product III-9a as a yellow powder, 0.32 g (32%). Analysis gave the following results.

NMR ($d_6DMSO+CDCl_3$) d 8.5 (s, 1H, $C_7$-H); 8.31 (d, 1H, NHC); 7.6 (d, 1H, 4'-H); 6.80 (d, 1H, 3'-H); 6.32 (broad s, 2H, $NH_2$); 4.54 (m, 1H, CHNH); 4.18 (m, 4H, 2 x $OCH_2$); 3.28 (m, $C_9$-$H_2$); 2.42 (t, 2H, glu $C_4$-$H_2$); 2.13 (m, 2H, glu $C_3$-$H_2$); 1.28 (m, 6H, 2 x $CH_3CH_2$).

Beta-(2,4-Diaminopyrimidino[4,5-β]pyrazin-6-yl)-5-ethyl-2-thenoyl-glutamic Acid (III-10a, Compound No. 5)

A mixture of the diester III-9a (0.26 g., 0.5 mmol) in 2-methoxyethanol (5 mL) was treated with water (5 mL) and 10% sodium hydroxide (5 mL). The mixture was stirred for one hour then adjusted to pH 5.5 with 2-N hydrochloric acid and concentrated under high vacuum. The residue was digested in water (5 mL) and the mixture was filtered. The resulting solid was washed with water and dried in vacuo at room temperature, giving 0.19 g (82%) of product III-10a. Analysis gave the following results.

HPLC shows 96.4% purity. UV (0,1N NaOH) 258 nm (28,310); 372 nm (6,737). NMR ($d_6DMSO$) delta 8.67 (s, 1H, CT-H); 8.50 (d, 1H, NHCH); 8.00 (broad s, 2H, $NH_2$); 7.65 (d, 1H, 4'-H); 6.90 (broad s, 3H, 3'-H+$NH_2$); 4.30 (m, 1H, CHNH); 3.42 (m, $C_9$-$H_2$+$C_{10}$-$H_2$); 2.35 (t, 2H, glu-$C_4$-$H_2$); 1.95 (m, 2H, glu $C_3$-$H_2$). Mass spectrum m/e 734 ($TMS_4$) (M+H). Anal. Calcd. for $C_{18}H_{19}N_7O_5S \cdot 2H_2O$: C, 44.90%; H, 4.81%; N, 20.36%. Found: C, 44.68%; H, 4.39%; N, 20.32%.

EXAMPLE 5

N-[Alpha-ethyl-beta-(2,4-diamino-[4,5,-β)-pyrazin-6-yl)-5-ethyl-2-thenoyl]-Glutamic Acid This example illustrates a preparation of N-[alpha-ethyl-beta-(2,4-diamino-[4,5-b)-pyrazin-6-yl)-5-ethylthiophene-2-carbonyl]-glutamic Acid (III-10b) according to the procedure illustrated in the Reaction Scheme 3. The compound is listed in Table 1 as compound 6.

Alpha-Ethyl-2-carbomethoxythiophene-5-acetic Acid Methyl Ester (III-5b)

A suspension of sodium hydride (0.59 g, 12.2 mmol) in 20 mL of dry dimethyl formamide was cooled to 0° C. A solution of III-5a (2.60 g, 12.2 mmol) in 20 mL of dry dimethyl formamide was added, and the reaction was stirred for an additional hour at 0° C. The reaction was cooled to −30° C. and treated dropwise with a solution of ethyl iodide (1.9 g, 12.2 mmol) in dry dimethyl formamide, then stirred for 2.5 hours at 20° C. The solution was neutralized to pH 8 by adding solid carbon dioxide, then concentrated under high vacuum. The residue was digested in ether (250 mL) and filtered. The filtrate was washed with water, followed with saturated sodium bicarbonate, then with 10% sodium bisulfite and then with water again. The organic layer was dried on magnesium sulfate and concentrated. The residue was chromatographed on flash silica gel using ethyl acetate/hexane as an eluent, to yield 1.7 g (58%) product III-5b as a clear, colorless oil. Analysis gave the following results.

TLC (10% ethyl acetate in hexanes on silica gel plate), Rf=0.35. NMR ($CDCl_3$) delta 7.59 (d, 1H, Ar 3-H); 7.20 (d, 1H, Ar 4-H); 3.81 (m, 7H, 2 x $OCH_3$+ARCH); 2.06 (m, 2H, $CH_2CH_3$); 0.95 (t, 3H, $CH_3CH_2$).

Beta-(2,4-Diaminopyrimido[4,5-β]pyrazin-6-yl)]-alphacarbomethoxy-alpha-ethyl-5-ethyl-2-carbomethoxythiophene (III-6b)

A mixture of sodium hydride (0.4 g, 8.3 mmol) in dry dimethyl formamide (25 mL) was cooled to 0° C. and treated dropwise with a solution of the diester III-5b (2.0 g, 8.3 mmol) in dry dimethyl formamide (25 mL), stirred at 0° C. for one hour, then cooled to −30° C. A solution of 2,4-diamino-6-bromomethylpteridine hydrobromide (2,7 mmol) in dimethylformamide (50 mL) was added dropwise, maintaining a −25° C. internal temperature, then stirred an additional 2.5 hours while warming to room temperature. The reaction was then adjusted to pH 8 with carbon dioxide and concentrated under a high vacuum to yield a yellow residue that was stirred in ether. Filtration gave a yellow solid which was washed with water and dried in vacuo to yield 0.97 g (85%) of product III-6b. Analysis gave the following results.

NMR (d$_6$DMSO) delta 8.35 (s, 1H, CT-H); 7.78 (broad s, 1H, NH); 7.65 (d, 1H, C$_4'$-H);7.17 (d, 1H, C$_3'$-H); 6.65 (broad s, 2H, NH$_2$); 6.52 (broad s, 1H, NH); 3.77 (s, ArCOOOCH$_3$); 3.68 (s, CCOOCH$_3$); 2.06 (m, 2H, CH$_2$CH$_3$); 0.76 (t, 3H, CH$_3$CH$_2$). Mass spectrum m/e 416 (M+H).

Beta-(2,4-Diaminopyrimidino[4,5-$\beta$]pyrazin-6-yl) alpha-carboxy-alpha-ethyl-5-ethylthiophene-2-carboxylic Acid (III-7b)

A mixture of the diester III-6b (0.95 g, 2.3 mmol) in 2-methoxyethanol (15 mL), water (15 mL), and 15 mL of 10% sodium hydroxide (15 mL) was stirred for 3.5 hours. The solution was adjusted to pH 5 by dropwise addition of 2N HCl, and the resulting mixture was concentrated under high vacuum. The residue was digested in water, then filtered to yield a cream-colored solid that was washed with water, then dried in vacuo at room temperature, giving 0.51 g (58%) of product III-7b. HPLC (see above conditions) showed 97% purity.

Beta-(2,4-diaminopyrimido [4,5,-$\beta$]pyrazin-6-yl-alphaethyl-5-ethylthiophene-2-carboxylic Acid (III-Sb)

A solution of the dicarboxylic acid III-7b (0.22 g, 0.57 mmol) in dry dimethylsulfoxide (10 mL) was heated to 125° C. for 30 minutes. The amber solution was then concentrated under high vacuum, and the residue was washed thoroughly with ether, then suspended in water (10 mL). Sufficient ammonium hydroxide was added to bring about solution, then adjusted to pH 5 with hydrochloric acid and filtered. The resulting tan solid was washed with water, then dried in vacuo, yielding 0.14 g (70%).

HPLC indicated 90.5% purity. Analysis gave the following results. UV (0.1N NaOH) 256 nm (28.546), 372 (7,300). Mass spectrum (DCl-NH$_3$) 561 (TMS$_3$)=345 (M+H). Anal Calcd for C$_{15}$H$_{16}$N$_6$O$_2$S . 0.6 H$_2$O: C, 50.72%; H, 4 88%; N, 23.66% Found: C, 50.54%; H, 4 94%; N 23 91%.

N-[alpha-Ethyl-beta-(2,4-diamino-[4,5-$\beta$]-pyrazin-6-yl)- 5-ethyl-2-thenoyl-glutamic Acid Diethyl Ester (III-9b)

A mixture of the carboxylic acid III-Sb (0.99 g, 2.9 mmol) and triethylamine (2.7 g, 26.7 mmol) in dry N,N-dimethylformamide (50 ml) was stirred at room temperature for 1 hour, then treated with isobutyl chloroformate (0.81 g, 5.9 mmol). The mixture was stirred for 1 hour, treated with L-glutamic acid diethyl ester hydrochloride (1.42 g, 5.9 mmol), and stirred at room temperature for 2 hours. Isobutyl chloroformate (0.41 g, 3.0 mmol) was added and the mixture was stirred at room temperature for 1 hour. L-glutamic acid diethyl ester hydrochloride (0.72 g, 3.0 mmol) was added and the mixture was stirred at room temperature for 1 hour. Isobutyl chloroformate (0.41 g, 3.0 mmol) was added and the mixture was stirred for 1 hour. L-glutamic acid diethyl ester hydrochloride (0.42 g, 3.0 mmol) was added and the reaction mixture was stirred at room temperature for 16 hours. The mixture was concentrated under high vacuum. The yellow solid was washed with water then dried in vacuo. Chromatography on flash silica gel (2% methanol in chloroform eluent) gave the product III-9a as a yellow foam in 20% yield (0.3g). Analysis gave the following results.

NMR (CDCl$_3$): delta =0.90 (t, 3 H C,0-CH$_2$-CH$_3$); 1.30 (m, 6 H, 2 X OCHC$_2$CH$_3$); 2.17 (m, 2 hours, glu C$_3$-H$_2$); 2.47 (m, 2 hours, glu C$_4$-H$_2$); 3.20 (m, 3 H, C$_9$-H$_2$+C$_{10}$-H); 4.16 (m, 4 H, 2 X OCH$_2$); 4.75 (m, 1 hour, CHNH); 5.45 (broad s, NH); 6.55 (m, 1 hour, C$_3$-H); 6.95 (m, 1 hour, NHCH); 7.30 (d, 1 hour, C$_4$-H); 8.41 (d, 1 hour, CTH). Anal. Calcd. for C$_{24}$H$_{31}$N$_7$O$_5$S . 0.7 H$_2$O: C, 53.16%; H, 5.93%; N, 18.08; Found: C, 53.43%; H, 5.79; N, 17.73%.

N-[alpha-Ethyl-beta-(2,4-diamino-[4,5-$\beta$]-pyrazin-6-yl)- 5-ethylthiophene-2-carbonyl]-glutamic Acid (III-10b, Compound No. 6)

A solution of the diester III-9b (0.55 mmol) in 2-methoxyethanol (10 ml) was treated with 10% sodium hydroxide (5 ml) and water (5 ml). After stirring for 75 minutes the solution was neutralized to pH 5 with 2M hydrochloric acid and concentrated under high vacuum. The residue was treated with water and the mixture filtered. The yellow solid was dried in vacuo, yielding 0.15 g (57%) of product III-10b.

HPLC 96.9% purity. Analysis gave the following results. UV (0.1 N, NaoH) 256 nm (28, 139), 371 (6, 810); mass spectrum m/e 762 (TMS$_4$M+H).

EXAMPLE 6

10-Allyl-10-Deazaaminopterin

This example illustrates a preparation of 10-allyl-10-deazaaminopterins according to procedure illustrated in the Reaction Scheme 4.

$\alpha$-Allylhomoterephthalic Acid Dimethyl Ester (IV-1a)

A mixture of 35% potassium hydride oil suspension (6.04 g, 35% w/w/, 53 mmols of potassium hydride) in 240 mL of sieve dried tetrahydrofuran was cooled to 0° C. The cold mixture was treated with homoterephthalic acid dimethyl ester (10.0 g, 48 mmols). The mixture was stirred at 0° C. for one hour. Allyl bromide (6.41 g, 53 mmols) was added and the mixture was stirred at 0° C. for 30 minutes, then at room temperature for 16 hours. The resulting mixture was treated with 4.8 mL of 50% acetic acid, then poured into 480 mL of water. The mixture was extracted with ether (2 ×250 mL). The ether extracts were combined, dried over magnesium sulfate, and concentrated to a brown oil. Chromatography on 250 g of flash silica gel (10% ether in hexane eluent) gave the product IV-1a as a pale yellow oil, 10.5 g (89% yield).

$^1$H NMR (CdCl$_3$): delta 7.69 (q, 4H, Ar); 5.64 (m, 1H, CH=CH$_2$; 5.09 (m, 2H, CH$_2$=CH); 3.80 (m, 7H, 2 x CH$_3$O/ArCH); 2.75 (m, 2H, CH$_2$CHAr).

10-Allyl-10-carbomethoxy-4-deoxy-4-amino-10-deazapteroic Acid Methyl Ester (IV -2a).

A mixture of potassium hydride in oil (2.43 g, 35% w/w, 21.2 mmols) in dry dimethylformamide (25ml) was cooled to −5° C. The cold mixture was treated, dropwise, with a solution of $\alpha$-allylhomoterephthalic acid dimethyl ester (IV-la) (5.25 g, 21.2 mmols) in dry dimethylformamide (25 ml) then stirred at 0° C. for 45 minutes. After cooling to −20° C., a solution of 2,4-diamino-6-bromomethylpteridine hydrobromide 0.2 isopropanol (2.45 g, 7.06 mmols) in dry dimethylformamide (40 ml) was added dropwise, maintaining a −20°

C. reaction temperature. The temperature was allowed to rise to 20° C. and was stirred for 2.5 hours. The reaction was then adjusted to pH 8 by addition of solid carbon dioxide. Concentration under high vacuum gave a residue which was dissolved in chloroform. This solution was washed with water, dried, and concentrated. The residue was washed with ether and dried in vacuo giving 2.2 g (74% yield) of product IV-2a.

Thin layer chromatography (10% methanol in chloroform on silica gel plates) showed a single spot, Rf 0.4. Mass spectrum m/e 423 (M / H). $^1$H NMR (CdCl$_3$): delta 8.45 (s, 1H, 7-H), 8.03 (d, 2H, C$_6$H$_4$), 7.37 (d, 2H, C$_6$H$_4$), 5.50 (m, CH=CH$_2$), 4.95 (m, 2H, CH$_2$=CH), 3.90 (s, 3H, ArCOOCH$_3$), 3.60 (m, 5H, C-10 COOCH$_3$-C-9 CH$_2$), 2.83 (m, 2H, CH$_2$CH=CH$_2$).

10-Allyl-10-carboxy-4-deoxy-4-amino-10-deazapteroic Acid (IIIa)

A solution of the dimethyl ester (IV-2a) (2.0 g, 4.7 mmols) in 2-methoxyethanol (2 ml) was treated with water (2 ml) then 10% sodium hydroxide (2 ml). The solution was stirred at room temperature for 24 hours. The solution was adjusted to pH 6 with acetic acid and concentrated under high vacuum to give a residue which was then dissolved in water (10 ml). Further acidification to pH 3 resulted in a precipitate which was collected, washed with water and dried in vacuo to yield 1.53 g (81%) of yellow solid product IV-3a.

HPLC indicated 90% purity. Mass spectrum m/e 395 (M+H); UV (0.1N NaOH): π max 255 nm (28,194), 368 (7,444).

10-Allyl-4-deoxy-4-amino-10-deazapteroic Acid/IV-4a)

A solution of the dicarboxylic acid (IV-3a) (0.26 g) in dry dimethyl sulfoxide (10 ml) was placed in a preheated 142° C. oil bath for 10 minutes. The solution was cooled to 35° C. and concentrated under high vacuum. The residue was triturated with ether to yield a tan solid, 0.23 g, 99% yield of product IV-4a.

HPLC indicated 95% purity. Mass spectrum m/e 351 (M+H).

10-Allyl-10-Deazaaminopterin Diethyl Ester (IV-5a)

A solution of the acid (IV-4a) (0.87 g, 2.5 mmols) in dry dimethyl formamide (25 ml) was treated with triethylamine (1.4 ml, 1.01 g, 9.96 mmols). After stirring at room temperature for 20 minutes, the solution was treated with isobutyl chloroformate (0.5 ml, 0.53 g, 3.9 mmols). The mixture was stirred at room temperature for one hour then treated with L-glutamic acid diethyl ester hydrochloride (0.96 g, 4.0 mmols). After stirring for 1.5 hours isobutyl chloroformate (0.5 ml) was again added. The mixture was stirred for one hour, then again treated with L-glutamic acid diethyl ester hydrochloride (0.96 g). After 1.5 hours, the process was repeated with isobutyl chloroformate (0.5 ml) and L-glutamic acid diethyl ester hydrochloride (0.96 g) and the final mixture stirred at room temperature for 16 hours. The reaction mixture was concentrated under high vacuum and the residue dissolved in chloroform, washed with water, then saturated with sodium bicarbonate. The organic layer was dried over magnesium sulfate and concentrated in vacuo. The residue was chromatographed on flash silica gel (2% methanol in chloroform) to yield a pure product IV-5a in 30% yield as shown by thin layer chromatography (10% methanol in chloroform on silica gel plates).

$^1$H NMR (CdCl$_3$):68.40 (s, 1H, 7-H), 7.75 (m, 2H, C$_6$H$_4$), 5.63 (m, 1H, CH=CH$_2$, 4.15 (m, 5H, 2 x CH$_2$CH$_3$/CHN), 3.20 (m, 3H, 9-H$_2$/10-H), 2.20 (m, 6H, CH$_2$CH=CH$_2$/ glu 3-H$^2$/glu 4-H$^2$), 1.25 (m, 6H, 2 x CH$_3$CH$_2$),

10-Allyl-10-deazaaminopterin/IV-6a)

The diethyl ester (IV-5a) (0.3 g, 0.56 mmols) was dissolved in 2-methoxyethanol (3 ml) and the solution was treated with water (3 ml) then 10% sodium hydroxide (3 ml). The solution was stirred for one hour at room temperature. The reaction mixture was neutralized to pH 5 with acetic acid. Concentration under high vacuum gave a residue which was dissolved in water (5 ml). Further adjustment to pH 3 gave a precipitate which was collected. The tan solid was washed with water and dried in vacuo giving 0.10 g (37%) of product IV-6a.

Mass spectrum m/e 489 (M+H). UV (0.1N NaOH) λ max 255 (27,330), 371 (6403); HPLC indicated 94% purity.

EXAMPLE 7

10-Proparqyl-10-Deazaaminopterin

This example illustrates a preparation of 10-propargyl-10-deazaaminopterin compound IV-6b according to procedure illustrated in the Reaction Scheme 4.

α-Propargylhomoterephthalic Acid Dimethyl Ester (IV-1b)

A mixture of 35% potassium hydride in oil (6.04 g, 35% w/w, 53 mmols of potassium hydride) in 240 mL of sieve dried tetrahydrofuran was cooled to 0° C. The cold mixture was treated with homoterephthalic acid dimethyl ester (10.0 g, 48 mmols). The mixture was stirred at 0° C. for one hour. Propargyl bromide (53 mmols) was added and the mixture stirred at 0° C. for 30 minutes, then at room temperature for 16 hours. The resulting mixture was treated with 4.8 mL of 50% acetic acid, then poured into 480 mL of water. The mixture was extracted with ether (2×250 mL). The ether extracts were combined, dried over magnesium sulfate, and concentrated to a brown oil. Chromatography on 250 g of flash silica gel (10% ether in hexane eluent) gave the product IV-1b as a white solid mp 63°–65° C.

Mass spectrum m/e 247 (M+H). IR (nujol C≡C-H, 3268 cm$^{-1}$. -$^1$H NMR (CDCl$_3$):68.05 (d, 2H, C$_6$H$_4$), 7.40 (d, 2H, C$_6$H$_4$), 3.91 (s, 3H, ArCOOCH$_3$), 3.88 (dd, 1H, ARCH), 3.71 (s 3H, —CHCOOCH$_3$), 2.95 (dddd, 1H, CH$_2$), 2.64 (dddd, 1H, CH$_2$), 1.96 (dd, 1H, C≡CH). Anal. Calcd, for C$_{14}$H$_{14}$O$_4$: C, 68.3; H, 5.73. Found: C, 68.0; H, 5.60.

10-Proparqyl-10-carbomethoxy-4-deoxy-4-amino-10-deazapteroic Acid Methyl Ester (IV-2b)

A mixture of potassium hydride (2.43 g, 35% w/w, 21.2 mmols) in dry dimethylformamide (25 ml) was cooled to −5° C. The cold mixture was treated, dropwise, with a solution of propargylhomoterephthalic acid dimethyl ester (IV-1b) (21.2 mmols) in dry dimethylformamide (25ml), then stirred at 0° C. for 45 minutes. After cooling to −20° C., a solution of 2,4- diamino-6-bromomethylpteridine hydrobromide 0.2 isopropanol (2.45 g, 7.06 mmols) in dry dimethylformamide (40 ml) was added, dropwise, maintaining a −20° C. reaction temperature. The temperature was allowed to rise to 20° C. and was stirred for 2.5 hours. The reaction was then adjusted to pH 8 by addition of solid carbon dioxide. Concentration under high vacuum gave a residue which, however, was not soluble in common organic solvents, and was therefore carried unpurified into the next step. The purity was acceptable by thin layer chromatographic analysis. The crude weight recovery of the product IV-2b was 90%. Mass spectrum m/e 420.

10-Propargyl-10-carboxy-4-deoxy-4-amino-10-deazapteroic Acid (IV-3b)

A solution of the dimethyl ester (IV-2b) (4.7 mmols) in 2-methoxyethanol (2 ml) was treated with water (2 ml) then 10% sodium hydroxide (2 ml). The solution was stirred at room temperature for 24 hours. The solution was adjusted to pH 7–8 with acetic acid and concentrated under high vacuum to give a residue which was then dissolved in water (10 ml). Further acidification to pH 6 resulted in a precipitate which was collected, washed with water and dried in vacuo. HPLC analysis indicated 92% purity after re-precipitation of the product from basic solution. The product IV-3b was obtained as a white solid in 75% yield.

Mass spectrum m/e 680 (M+H as the TMS$_4$ derivative).

10-Proparqyl-4-deoxy-4-amino-10-deazapteroic Acid (IV-4b)

Three decarboxylations of IV-3b were conducted on 86, 86, and 55 mg of material. In each case the reaction aliquot was dissolved in 3 ml of dimethyl sulfoxide and immersed for a period of five minutes in an oil bath preheated to 123° C. The reactions were combined and the solvent removed in high vacuum. The residue was precipitated twice from dilute ammonium hydroxide solution by addition of acetic acid. HPLC analysis indicated 85% purity with no impurity exceeding 4%. The product IV-4b was a tan solid (29% yield). Mass spectrum 564 (M+H as the TMS$_3$ derivative).

10-Propargyl-10-deazaminopterin Diethyl Ester (IV-5b)

A solution of the acid (IV-4b) (0.87 g, 2.5 mmols) in dry dimethyl formamide (25 ml) was treated with triethylamine (1.4 ml, 1.01 g, 9.96 mmols). After stirring at room temperature for 20 minutes, the solution was treated with isobutyl chloroformate (0.5 ml, 0.53 g, 3.9 mmols). The mixture was stirred at room temperature for one hour then treated with L-glutamic acid diethyl ester hydrochloride (0.96 g). After 1.5 hours the process was repeated with isobutyl chloroformate (0.5 ml) and L-glutamic acid diethyl ester hydrochloride (0.96 g) and the final mixture stirred at room temperature for 16 hours. The reaction was concentrated under high vacuum and the residue dissolved in chloroform, washed with water, then with saturated sodium bicarbonate. The organic layer was dried over magnesium sulfate and concentrated in vacuo. The residue was chromatographed on flash silica gel (2% methanol in chloroform).

Following chromatography, an aliquot was saponified. HPLC analysis indicated 93% purity. The product IV-5b was obtained in a yellow foam in 55% yield. Mass spectrum m/e 534 (M+H). $^1$H NMR (CdCl$_3$): delta 8.5 (s, 1h 7-H), 7.75 (d, 2H, C$_6$H$_4$), 7.28 (d, 2H, C$_6$H$_4$), 7.0 (br s, 1H, NH), 5.35 (br s, 1H, NH), 4.77 (m, 1H, NHCH), 4.10 and 4.25 (q, 4H, OCH$_2$), 3.46 (m, 2H, C-9CH$_2$), 3.23 (m, 1H, C-10H), 2.62 (m, 2H, C≡CCH$_2$), 2.46 (m, 2H, CH$_2$COOEt), 2.15 and 2.32 (m, 2H, glu-3CH$_2$), 2.04 (brS, 1H, C≡CH), 1.33 and 1.29 (t, 6H, CH$_2$CH$_3$).

10-Propargyl-10-deazaminopterin (VI-6b)

The diethyl ester (IV-Sb) (0.3 g, 0.56 mmols) was dissolved in 2-methoxyethanol (3ml) and the solution was treated with water (3 ml) then 10% sodium hydroxide (3 ml). The solution was stirred for one hour at room temperature. The reaction mixture was neutralized to pH 5 with acetic acid. Concentration under high vacuum gave a residue which dissolved in water (5 ml). Further adjustment to pH 3 gave a precipitate which was collected. The product IV-6b was obtained as a pale yellow solid in 72% yield.

HPLC analysis indicated 95% purity. Mass spectrum m/e 765 (as the TMS3 derivative). UV (0.1N NaOH) 2max 256 (ε29,800), 372 (ε7000). Anal. Calcd for C$_{23}$H$_{23}$N$_7$O$_5$ H$_2$O C, 52.9; H, 5.40; N, 18.8. Found: C, 52.8, H, 5.17; N, 18.4.

EXAMPLE 8

Tablet Formulation

This example illustrates preparation of compounds of the current invention in a tablet form.

| Composition | mg/Tablet |
| --- | --- |
| Heteroaroyl-10-deazaaminopterin | 15 |
| Lactose | 86 |
| Cornstarch (dried) | 45.5 |
| Gelatin | 2.5 |
| Magnesium stearate | 1.0 |

The method of preparation is identical with that of Example 1, except that 60 mg of starch is used in the granulation process and 20 mg during tableting.

Using the same procedure, 10-alkynyl and 10-alkenyl-deazaaminopterins are formulated as tablets.

EXAMPLE 10

Capsule Formulation

This example illustrates preparation of compounds of the current invention in a capsule form.

| Capsule Composition | mg/Capsule |
| --- | --- |
| Heteroaroyl-10-deazaaminopterin | 250 |
| Lactose | 150 |

The heteroaroyl-10-deazaaminopterin compound and lactose are passed through a sieve and the powders well mixed together before filling into hard gelatin capsules of suitable size, so that each capsule contains 400 mg of mixed powders.

Using the same procedure, 10-alkynyl and 10-alkenyl-deazaaminopterins are formulated as capsules.

EXAMPLE 11

Suppositories

This example illustrates preparation of compounds of the current form as suppositories.

| Composition | mg/suppository |
| --- | --- |
| Heteroaroyl-10-deazaaminopterin | 50 |
| Oil of theobroma | 950 |

The heteroaroyl-10-deazaaminopterin compound is powdered and passed through a sieve and triturated with molten oil of theobroma at 45° C. to form a smooth suspension.

The mixture is well stirred and poured into molds, each of nominal 1 g capacity, to product suppositories.

Using the same procedure, 10-alkynyl and 10-alkenyl-deazaaminopterins are formulated as cachets.

EXAMPLE 12

10-Deazaaminopterins Formulated as Cachets

This example illustrates formulation of compounds of the current invention into cachets.

| Composition | mg/Cachet |
|---|---|
| Heteroaroyl-10-deazaaminopterin | |
| Lactose | 400 |

The heteroaroyl-10-deazaaminopterin compound is passed through a mesh sieve, mixed with lactose previously sieved and fitted into cachets of suitable size so that each contains 500 mg.

Using the same procedure, 10-alkynyl-10-alkenyl-diazaaminopterins are formulated as tablets.

EXAMPLE 13

This example illustrates a preparation of compounds of the current invention in injection forms.

| Composition Intramuscular injection | mg/Injection |
|---|---|
| Heteroaroyl-10-deazaaminopterin | 10 |
| Sodium carboxymethylcellulose | 2.0 |
| Methyl paralpha-hydroxybenzoate | 1.5 |
| Propyl para-hydroxylbenzoate | 0.2 |
| Water for injection to 1.0 ml | |

Other injection forms such as intraperitoneal, intravenous subcutaneous are prepared similarly.

The compound of the invention and the other excipients, listed above, were dissolved in a sterile solution in an aqueous carrier system. Using the same procedure, 10-alkynyl, and 10-alkenyl-deazaaminopterins are formulated as injections.

EXAMPLE 14

Antiarthritic effect of Heteroaroyl-10-Deazaaminopterin in Mammals

This example illustrates the antiarthritic activity of the compounds of the current invention in mammals.

The study used a mouse model of inflammatory disease that occurs in response to an antigenic challenge with Type II collagen according to method described in *Nature*, 283, 666–668 (1890).

DBA/1 mice were immunized with a suspension of fetal bovine Type II collagen (1 mg/ml) prepared in complete Freund's adjuvant. The primary injection was given using 0.1 ml of the collagen emulsion giving a total of 0.1 mg of Type II collagen per mouse. The animals were given a booster injection of Type II collagen (100 μg in 0.01M acetic acid) on day 21 by intraperitoneal injection.

The results of the in vivo testing of methotrexate showed that using prophylactic regimens in which drug administration was initiated two days prior to administration of antigen (Type II collagen) was more effective than starting drug at day 19, two days prior to the first and only boost with Type II collagen. In this model the untreated positive control animals have an incidence of arthritis ranging from 90% to 100% of injected animals at day 44.

The effect of methotrexate and test compounds on the extent of inflammation was determined by visual observation and by direct analysis of paw swelling using caliper measurements. The results are summarized in Table II, and show a direct correlation between the decrease in the number of animals having disease and a decrease in the extent of inflammation, as determined by paw swelling.

The following data illustrate administration to mice of compounds 1,2,5,and 6 of Table 1, of the invention and 10-allyl-10-deazaminopterin and the effect compared to the known antiarthritic drug methotrexate in the evaluation of the compounds antiinflammatory activity. The data are presented as two separate measurements: the visually observed presence of inflammation in the mouse, and the caliper-measured degree of swelling of the rear paws of the mouse.

TABLE 2

| Compound | | Dose mg/kg | No mice affected on day indicated[b] | | | Avg. thickness of rear paws (mm) over days 30–44[c] | |
|---|---|---|---|---|---|---|---|
| | | | Day 30 | Day 37 | Day 44 | Treated | Untreated |
| None | | | 31/43 | 38/43 | 41/43 | | 2.29–2.73 |
| 1 | R = H X = | 18.0 | 0/8 | 1/8 | 2/8 | 2.14–2.38 | |
| 2 | R = C2H5 X = | 15.0 | 0/8 | 1/8 | 1/8 | 2.15–2.26 | |
| 5 | R = H X = | 8.0 | 3/8 | 2/8 | 4/8 | 2.22–2.33 | |
| 6 | R = C2H5 X = | 2.5 | 2/8 | 6/8 | 6/8 | 2.18–2.75 | |
| 10 | 10-Allyl-10-deazaminopterin | 12 | 1/8 | 5/8 | 4/8 | 2.19–2.35 | |
| MTX[a] | | 9.0 | 1/22 | 1/22 | 6/22 | 2.18–2.34 | |

[a]MTX and untreated controls are composites from multiple runs.
[b]Visual evidence of inflammation.
[c]Values in parentheses are 30 day and 44 day measurements vs. equivalent for untreated controls; decrease in inflammation vs. control is most notable at day 44.

It is apparent from the above results that the number of test mice affected was considerably decreased by administration of the heteroaroyl-10-deazaaminopterin compound. The results show that heteroaroyl-10- deazaaminopterin compounds on a similar dosage level are at least as effective as methotrexate. The antiinflammatory activity of methotrexate is accepted as an effective comparative standard for determination of the antiinflammatory activity of other compounds. Therefore, the heteroaroyl-10-deazaaminopterins compounds are expected to be at least as effective as methotrexate, under similar conditions. The potent anti-arthritic activity of the heteroaroyl-10-deazaaminopterin compounds tested is evident from the results.

EXAMPLE 15

Effect of 10-Proparqyl-10-Deazaaminopterin on Murine Leukemia Cells

This example illustrates the evaluation of the effect of 10-propargyl-10-deazaaminopterin on growth inhibition of L 1210 murine leukemia cells in culture and for its ability to inhibit dihydrofolate reductase derived from L 1210 cells.

The used method was that described in *Biochem. Pharmacol.*, 28:2993–2997 (1973). Enzyme was derived from L 1210 murine leukemia cells. The inhibition was conducted at pH 7.3. Data were analyzed according to the method described in *Biochem J.* 135:101–107 (1973). Methotrexate was used as a control.

Murine L1210 cells were obtained as intraperitoneal ascites suspensions from $BD2F_1$ mice. The cells were grown in RPM1 1640 medium supplemented with 10% fetal calf serum. Cultures in the logarithmic stage of growth were harvested, resuspended and exposed to test compounds at varying concentrations. Growth of controls was monitored to verify that the growth pattern was normal. At 72 hours, cell counts were taken and averaged and the means were plotted against drug concentration to determine the concentration causing 50% inhibition of cell growth.

In one set of studies, the effect of 10-allyl and 10-propargyl-10-deazaaminopterins on growth inhibition of L1210 leukemia cells was determined and compared with the effect of methotrexate. Results are shown in Table 3.

TABLE 3

| Compound | L/1210 Growth Inhibition IC$_{50}$ nM |
|---|---|
| 10-Allyl-10-deazaminopterin | 4.30 |
| 10-Propargyl-10-deazaminopterin | 2.0 |
| Methotrexate | 9.5 |

As seen from the Table 3, under these circumstances, 10-propargyl-10-deazaaminopterin was more than 4.5 times as effective in inhibiting the growth of L1210 leukemia cells than methothrexate and more than twice as active than corresponding 10-allyl-10-deazaminopterin.

When the effect of 10-propargyl-10-deazaaminopterin on the inhibition of dihydrofolate reductase derived from 1210 leukemia cells was studied, as shown in Table 4, it was found to be one-third as potent as MTX for enzyme inhibition. This was consistent with extension of chain length beyond two carbon units. However, as seen above, the propargyl compound was nearly 5-fold more potent than MTX as an inhibitor of growth in L1210 cells. This result prompted a measurement of the transport properties for facilitated entry into the L1210 cells vs MTX. As seen from Table 4, 10-fold transport advantage vs MTX for influx $K^1$ was observed as determined by competitive binding for the transport protein.

TABLE 4

| Compound | DHFR Inhibn: ($K^i$) | Growth Inhibn: IC$_{50}$, $\mu M^b$ | Transport Influx: $K_i$, $\mu M^b$ |
|---|---|---|---|
| IV-6b 10-Propargyl-10-DA | 18.2 ± 4.0 | 2.0 | 0.45 ± 0.1 |
| MTX | 5.75 ± 1.0 | 9.50 | 4.2 ± 0.5 |

EXAMPLE 16

Antitumorigenic Effect of 10-Propargyl-10-Deazaaminopterin

This example illustrates the effect of 10-propargyl-10-deazaaminopterin in suppression of the tumor growth.

The propargyl compound was evaluated in the EO771 murine mammary tumor model in vivo according to method described in *Proc. Ann. Soc. Clin. Oncol.*, 11:51 (1992)

Tumor evaluation was performed in EO771 solid subcutaneous mammary tumor in BDF1 female mice. The mice were injected with tested compound on the third day post tumor development with doses as indicated in Table 4.

At a dose of 36 mg/kg compound IV-6b totally suppressed the growth of the tumor at the 14 and 21 day post treatment points. The compound was also effective at a 24 mg/kg dose at day 14, but some regrowth had commenced by day 21. At the 36-mg dose one completely tumor-free survivor was noted among the surviving animals. Methotrexate was not as effective in this assay at day 21 even at a dose of 9 mg/kg. This assay is indicative that compounds of this invention and their analogues are effective in suppression of the neoplastic growth. The EO771 solid tumor model is somewhat predictive for activity in human breast cancer as demonstrated by 10-ethyl-10-deazaminopterin (Edatrexate). This drug was highly effective in EO771 and has shown outstanding efficacy in the clinic with late-stage breast cancer.

TABLE 5

| E0771 Solid Mammary Tumor Evaluation in BDF1 Female Mice$^a$ | | | | |
|---|---|---|---|---|
| | | Average tumor vol (mm$^3$) | | |
| Dose (mg/kg)$^b$ | No. mice | day 10 (% T/C) | 14 | 21 |
| Control | 5 | 131 (100) | 1232 (100) | 2066 (100) |
| IV-6b (24) | 3 | 62 (47) | 19 (2) | 204 (100) |
| IV-6b (36) | 3 | 48 (31) | 6 (1) | 21 (1)$^c$ |
| MTX (3) | 5 | 113 (86) | 187 (15) | 1260 (61) |
| MTX (6) | 5 | 34 (26) | 19 (2) | 382 (18) |
| MTX (9) | 5 | 4 (3) | 19 (2) | 310 (15) |

$^a$Subcutaneous tumor.
$^b$Dose schedule day 3, QDX 5 (ip).
$^c$One mouse was tumor free of two survivors.

What is claimed is:

1. Heteroaroyl-10-deazaaminopterin compounds having the formula (I):

$$\text{(I)}$$

[structure: pteridine ring with NH$_2$ groups, connected to CH$_2$—CH—X—NHCH(COOH)CH$_2$CH$_2$COOH with R substituent]

wherein X is [one of and R is hydrogen or alkyl, alkenyl, or alkynyl having from one to eight carbon atoms.

2. The compounds of claim 1 wherein R is alkenyl having from three to eight carbon atoms.

3. The compounds of claim 1 wherein R is alkynyl having from three to eight carbon atoms.

4. The compounds of claim 1 wherein R is alkyl having from one to three carbon atoms.

5. The compounds of claim 4 wherein the alkyl is ethyl.

6. The compounds of claim 1 wherein X is

7. The compounds of claim 1 wherein X is

8. The compound of claim 1, namely N-[2,4-diaminopyrimido-[4,5-beta]-pyrazin-6-yl) -6-ethyl-nicotinoylglutamic acid.

9. The compound of claim 1, namely N-[alpha-ethyl-beta-[2,4-diaminopyrimido-[4,5-beta]-pyrazin-6-yl)-6-ethylnicotinoyl-]glutamic acid.

10. The compound of claim 1, namely beta-[2,4-diaminopyrimido-[4,5-beta]-pyrazin-6-yl) -6-ethyl-nicotinoylglutamic acid.

11. A method for treating arthritis and other proliferative diseases which comprises administering to a warm-blooded animal having an inflammation of the joints or other evidence of the diseases, a therapeutically effective amount of a heteroaroyl-10-deazaaminopterin compound having the formula (I)

wherein X is one of and R is hydrogen or alkyl, alkenyl, or alkynyl having from one to about eight carbon atoms.

12. The method of claim 11 wherein the compound is administered as a pharmaceutically acceptable salt thereof.

13. The method of claim 12 wherein the compound is administered in an amount with the range from about 0.1 to about 500 mg per day.

* * * * *

UNITED STATES PATENT AND TRADEMARK OFFICE
CERTIFICATE OF CORRECTION

PATENT NO. : 5,354,751
DATED : October 11, 1994
INVENTOR(S) : Joseph I. DeGraw, et al.

It is certified that error appears in the above-indentified patent and that said Letters Patent is hereby corrected as shown below:

Column 4, line 31, add a "-" between the number "10" and "d".

Column 9, line 57, replace "illustratesoa" with "illustrates a".

Column 10, Formula, lines 58-60, replace "$CH_2$" with "$CH_3$".

Column 11, II-4 of Reaction Scheme 2, Delete "∅2" and replace with $O_2$.

Column 14, line 68, replace "II" with "III".

Column 15, line 22, delete 15°.

Column 15, line 37, delete "5-carboxymethoxy-2-" and replace with "5-carbomethoxy-2-".

Column 15, line 68, delete "(I3a)" and replace with "(I-3a)".

Column 17, line 68, delete "(IIS) and replace with "II-8".

Column 19, lines 2 and 3, delete "(III-Sa)" and replace with "(III-8a)".

Column 21, line 11, delete "R-" and replace with "R=".

Column 21, line 36, between the words alkenyl and alpha, delete "of" and replace with "or".

Column 21, line 46, replace "at low" with "room temperature or 20-25°".

Column 22, lines 51 and 53, a "-" between the number "10" and "d".

Column 22, line 56, replace "test" with "in vitro".

UNITED STATES PATENT AND TRADEMARK OFFICE
CERTIFICATE OF CORRECTION

PATENT NO. : 5,354,751

DATED : October 11, 1994

INVENTOR(S) : Joseph I. DeGraw, et al.

It is certified that error appears in the above-indentified patent and that said Letters Patent is hereby corrected as shown below:

Column 23, line 5, replace "NH2" with "$NH_2$".

Column 25, lines 17-18, replace "I, !    )." with "(I-1)."

Column 25, line 44, replace "(CDC13)" with "($CDCl_3$)".

Column 25, line 55, replace "of I-I " with "I-1".

Column 26, lines 10, 31, and 57, replace "4,5-B" with "4,5-β".

Column 26, line 48, replace "Ph 5" with "pH 5".

Column 26, line 57, replace "6eth" with "6-eth".

Column 27, lines 24 and 25, delete "CI-7a) (Compound No. 1) and replace with (I-7a) Compound No. 1).

Column 27, line 60, delete "." before "for".

Column 27, line 66, replace "carbondioxide" with "carbon dioxide".

Column 28, line 37, replace "ESter" with "Ester".

Column 28, line 68, replace "/" with ".".

UNITED STATES PATENT AND TRADEMARK OFFICE
CERTIFICATE OF CORRECTION

PATENT NO. : 5,354,751
DATED : October 11, 1994
INVENTOR(S) : Joseph I. DeGraw, et al.

It is certified that error appears in the above-indentified patent and that said Letters Patent is hereby corrected as shown below:

Column 29, line 27, replace "III-9" with "II-9".

Column 29, line 29, replace "5" with "3".

Column 29, line 42, replace "11-3" with "II-3".

Column 30, line 29, replace "Cg" with "C$_9$".

Column 31, line 29, replace "5" with "3".

Column 31, line 31, replace "rag" with "mg".

Column 31, line 48, after "Scheme 3" add, --The compound is listed as 5 in Table 1--.

Column 33, lines 13, 26, 34, replace "Sa" with "8a".

Column 33, lines 65 and 66, replace "Compound No. 5) with "Compound No. 5).".

Column 34, lines 60, 63, and 66, delete "." after "C".

Column 35, lines 30 and 50, replace "Sb" with "8b".

Column 37, line 33, "Acid/" should read --Acid (--.

Column 38, line 7, "pterin/" should read --pterin (--.

Column 38, lines 23 and 53, replace "Proparqyl" with "Propargyl".

UNITED STATES PATENT AND TRADEMARK OFFICE
CERTIFICATE OF CORRECTION

PATENT NO.   :   5,354,751
DATED        :   October 11, 1994
INVENTOR(S)  :   Joseph I. DeGraw, et al.

It is certified that error appears in the above-indentified patent and that said Letters Patent is hereby corrected as shown below:

Column 39, line 25, replace "Proparqyl" with "Propargyl".

Column 40, line 5, replace "Sb" with "5b".

Column 41, line 6, replace "product" with "produce".

Column 42, under Table 2, first column of compound, replace "1" with "5", replace "2" with "6", replace "5" with "1", and replace "6" with "2".

Column 43, line 1, replace "on" with "of" after "compounds".

Column 43, line 13, replace "10-Proparqyl" with "10-Propargyl".

Column 44, line 68, delete "[one of "

Signed and Sealed this

Ninth Day of May, 1995

BRUCE LEHMAN

*Attest:*

*Attesting Officer*   Commissioner of Patents and Trademarks